United States Patent [19]

Buell et al.

[11] Patent Number: 5,769,838
[45] Date of Patent: *Jun. 23, 1998

[54] DISPOSABLE PULL-ON PANT

[75] Inventors: Kenneth Barclay Buell, Cincinnati; Edward Paul Carlin, Maineville, both of Ohio

[73] Assignee: The Procter & Gamble Company, Cincinnati, Ohio

[*] Notice: The term of this patent shall not extend beyond the expiration date of Pat. No. 5,569,234.

[21] Appl. No.: 738,136

[22] Filed: Oct. 25, 1996

Related U.S. Application Data

[63] Continuation of Ser. No. 713,054, Sep. 12, 1996, which is a continuation of Ser. No. 415,816, Apr. 3, 1995, Pat. No. 5,569,234.

[51] Int. Cl.$^6$ .................................................. A61F 13/15
[52] U.S. Cl. .................. 604/396; 604/385.1; 604/385.2; 604/358
[58] Field of Search ................................ 604/358, 385.1, 604/385.2, 392, 393, 394, 395, 396

[56] References Cited

U.S. PATENT DOCUMENTS

| | | |
|---|---|---|
| 3,156,242 | 11/1964 | Crowe, Jr. . |
| 3,246,754 | 4/1966 | Bierenbaum et al. . |
| 3,881,489 | 5/1975 | Hartwell . |
| 3,989,867 | 11/1976 | Sisson . |
| 4,059,114 | 11/1977 | Richards . |
| 4,205,679 | 6/1980 | Repke et al. . |
| 4,341,216 | 7/1982 | Obenour . |
| 4,355,425 | 10/1982 | Jones et al. . |
| 4,610,680 | 9/1986 | La Fleur . |
| 4,610,681 | 9/1986 | Strohbeen et al. . |
| 4,619,649 | 10/1986 | Roberts . |
| 4,641,381 | 2/1987 | Heran et al. . |
| 4,681,578 | 7/1987 | Anderson et al. . |
| 4,690,681 | 9/1987 | Haunschild et al. . |

(List continued on next page.)

FOREIGN PATENT DOCUMENTS

| | | |
|---|---|---|
| 0 104 906 | 4/1984 | European Pat. Off. . |
| 0 638 304 A1 | 2/1995 | European Pat. Off. . |
| 0 641 552 A1 | 3/1995 | European Pat. Off. . |
| 3-176053 | 7/1991 | Japan . |
| 1 144 674 | 3/1969 | United Kingdom . |
| 2 244 909 | 12/1991 | United Kingdom . |
| WO 93/17648 | 9/1993 | WIPO . |
| WO 93/24085 | 12/1993 | WIPO . |
| WO 94/28845 | 12/1994 | WIPO . |
| WO 95/03765 | 2/1995 | WIPO . |
| WO 95/06451 | 3/1995 | WIPO . |

*Primary Examiner*—John G. Weiss
*Assistant Examiner*—Francis K. Cuddihy
*Attorney, Agent, or Firm*—Steven W. Miller; E. Kelly Linman; Jacobus C. Rasser

[57] ABSTRACT

Pull-on garments provided with a continuous belt in the front region and the back region to distribute the forces generated during use in order to better fit the pull-on garment on the wearer. In a preferred embodiment, the pull-on garment comprises a chassis layer comprising a continuous sheet that defines a front region, a back region, and a crotch region; a first belt layer joined to the chassis layer in the front region; a second belt layer joined to the chassis layer in the back region; elastic panel members positioned between the belt layers and the chassis layers which laminate is mechanically stretched to form elastically extensible stretch laminates in both the front region and the back region in the side panels; and seams joining the front region to the back region so as to form the leg openings and waist openings. The continuous chassis layer and belt layers thus form the continuous belt of the pull-on garment. Because the belt layers extend continuously laterally across the waist region and do not cover the entire crotch region, and because the chassis layer is thus exposed in the crotch region, the pull-on garment has a unique aesthetic feature which consumers perceive as providing a cloth-like feel in the waist but the containment characteristics in the crotch.

16 Claims, 15 Drawing Sheets

U.S. PATENT DOCUMENTS

| | | |
|---|---|---|
| 4,710,189 | 12/1987 | Lash . |
| 4,743,239 | 5/1988 | Cole . |
| 4,743,241 | 5/1988 | Igaue et al. . |
| 4,900,317 | 2/1990 | Buell . |
| 4,940,464 | 7/1990 | Van Gompel et al. . |
| 5,021,051 | 6/1991 | Hiuke . |
| 5,114,418 | 5/1992 | Levy . |
| 5,171,239 | 12/1992 | Igaue et al. . |
| 5,236,430 | 8/1993 | Bridges . |
| 5,246,433 | 9/1993 | Hasse et al. . |
| 5,263,948 | 11/1993 | Karami . |
| 5,358,500 | 10/1994 | LaVon et al. . |
| 5,571,096 | 11/1996 | Dobrin . |

DISPOSABLE PULL-ON PANT

This application is a continuation of copending application Ser. No. 08/713,054 filed on Sep. 12, 1996, which is a continuation of application Ser. No. 08/415,816, now U.S. Pat. No. 5,569,234, filed on Apr. 3, 1995.

FIELD OF THE INVENTION

The present invention relates to disposable pull-on garments which are donned by inserting the wearer's legs into the leg openings and sliding the garment up into position about the lower torso. Examples of such disposable pull-on garments include disposable underwear, pull-on diapers, training pants, and disposable panties for menstrual use. The present invention more particularly relates to unitary disposable absorbent pull-on garments such as pull-on diapers, training pants, incontinent pull-on briefs, and the like, which provide improved wearer comfort, increased leakage protection, and sustained dynamic fit.

BACKGROUND OF THE INVENTION

Infants and other incontinent individuals wear disposable absorbent articles such as diapers to receive and contain urine and other body exudates. Absorbent garments having fixed sides (e.g., training pants or pull-on diapers) have become popular for use on children able to walk and often who are toilet training. In order to contain body exudates as well as to fit a wide variety of body shapes and sizes, these pants must fit snugly about the waist and legs of the wearer without drooping, sagging or sliding down from its position on the torso as well as fitting larger wearers without causing irritation to the skin due to the product being too tight. Thus, the pant must have elastic extensibility in the waist and legs with the elastic features providing a high degree of stretch.

Many training pants and pull-on diapers use conventional elastic elements secured in an elastically contractible condition in the waist and leg openings. Typically, in order to insure full elastic fit about the leg and the waist such as is provided with durable undergarments, the leg openings and waist opening are encircled with elasticized bands of rubber or other materials positioned along the curve of the opening. These pants are typically characterized as "balloon style" pants because of the contraction caused by the elasticized bands in specific zones of the product while the remaining material tends to blouse. Examples of such training pants are disclosed in U.S. Pat. No. 5,171,239 to Igaue, et al. on Dec. 15, 1992 and U.S. Pat. No. 4,610,681 to Strohbeen, et al. on Sep. 9, 1986. Although these pants will allow fit of various waist and leg sizes due to the fact that the contractive elastic openings will expand to accommodate various size wearers, these products still fit a limited range of fit sizes because the elastic elements are in contraction and do not have a high degree of stretch. The narrow elastic bands used in the waist opening and the leg openings also tend to concentrate the "fitment" forces in a narrow zone of the wearer's body leading to increased incidence of skin marking of the wearer. Further, the sides and remainder of the products are typically not elastically extensible thereby reducing the fit.

In order to solve this deficiency in balloon-style pants, some manufacturers have positioned elastic strands across the entire front and back regions of the product. For example, WO 93/17648 published on Sep. 16, 1993, discloses a pant-type diaper in which the front and/or the rear parts are elastically contractible and the ends of the absorbent core are disposed in these regions. These additional elastic strands act to contract the entire front and back waist parts of the pant including the end areas of the absorbent core. This allows greater expansion of the product in the waist region but causes the absorbent core to be gathered and bunch at the waist opening. This gathering and bunching results in a higher risk of leakage at the waist since channels are created along the absorbent core that allows body exudates to wick or flow out of the waist. This gathering of the absorbent core also affects the appearance of the product in that the product does not appear as aesthetically pleasing as the balloon style pants.

Another type training pant is shown in U.S. Pat. No. 4,940,464 issued to Van Gompel, et al. on Jul. 10, 1990, wherein a pant-like garment is formed by attaching discrete stretchable members to the side edges of the main body of the garment. This stretchable member allows the article to fit variations in size as the stretchable member expands to meet the size of the wearer. However, the seaming of the main body with the stretchable members are a major problem in the product and in the manufacturing process. The seams must be made extremely strong and capable of handling great forces during application and use. A pant undergoes severe forces and stresses during use which may cause the side panels to break away or tear from the main body portion. Further, controlling these separate stretchable members severely complicates the manufacturing process and causes these pants to be more costly to the consumer. The seams to the main body portion also tend to concentrate the fitment forces at the top and bottom of the product resulting in increased seam tearing and poorer fit of the garment.

U.S. Pat. No. 5,246,433 issued to Hasse, Bridges & Miller on Sep. 21, 1993, discloses a pant having stretch laminate side panels as well as elastic waistbands and leg bands. The stretch laminates in the side panels provide stretch in the sides of the product to better fit the pant on the wearer. The stretch laminates are unitary with the rest of the pant to overcome the drawbacks associated with the pants having separate and discrete elastic panel members attached thereto while improving the fit over the conventional balloon-style pants. However, these pants suffer from the drawback that the side panels are not sufficiently stretchable to allow a wearer to easily pull the pant on by themselves. The stretch laminates disclosed therein provide a limited amount of stretch. Further, the materials used to form the stretch laminates can have problems with tearing or shredding during use resulting in the products being scrapped by the manufacturer.

Another drawback with all of these products is the breathability of the product. The panels of the pant are typically formed by films or foams which can preclude the breathability of such products. This lack of breathability may result in a hot stuffy product for the wearer.

It is, therefore, an object of the present invention to provide a disposable pull-on garment with a high degree of stretch such that the garment will conformably fit wearers in a broad range of sizes.

It is a further object of the present invention to provide a disposable pull-on garment that can withstand the high wearer forces encountered during use while not binding the absorbent core, providing forces along the legs to accommodate the legs while not red marking, and providing a secure fit about the waist.

It is a still further object of the present invention to provide a disposable pull-on garment having a continuous belt which has various zones of elastic extensibility that will not bind the absorbent core while providing better fit at the waist and the legs.

It is a further object of the present invention to provide a disposable pull-on garment with a high degree of breathability in at least the side panels, and more preferably in the waistband zones, to allow vapor transmission so that the garment is not hot and stuffy.

SUMMARY OF THE INVENTION

The disposable pull-on garments of the present invention preferably are unitary disposable absorbent garments such as a pull-on diapers or training pants capable of withstanding the forces encountered during use while being relatively simple and cost effective to manufacture. The pull-on garment is provided with a continuous belt in the front region and the back region to distribute the forces generated during use in order to better fit the pull-on garment on the wearer. The continuous belt has a central panel comprising an elastically contractible waistband panel and a non-binding medial panel, extensible side panels on either side of the central panel, and seam panels such that the sides and upper central waist of the garment expand to allow the garment to be donned easily, move with the wearer during use, maintain the fit of the garment during use, and hold the absorbent core close to the body to better contain discharged exudates while not binding the absorbent core in a manner which increases the likelihood of leakage. In especially preferred embodiments, the pull-on garment is not uncomfortable for the wearer because it is provided with means which allow vapor transmission via vents or apertures or using breathable materials to form the garment.

In an especially preferred embodiment, the pull-on garment comprises a chassis layer comprising a continuous sheet that defines a front region, a back region, and a crotch region; a first belt layer joined to the chassis layer in the front region; a second belt layer joined to the chassis layer in the back region; and elastic panel members positioned between the belt layers and the chassis layer which laminate is mechanically stretched to form elastically extensible stretch laminates in both the front region and the back region in the side panels; and seams joining the front region to the back region so as to form the leg openings and waist openings. The continuous chassis layer and belt layers in conjunction with other elements thus form the continuous belt of the pull-on garment. Because the belt layers extend continuously laterally across the waist region and do not cover the entire crotch region, and because the chassis layer is thus exposed in the crotch region, the pull-on garment has a unique aesthetic feature which consumers perceive as providing a cloth-like feel in the waist and better containment characteristics in the crotch region. The pull-on garment also preferably comprises an elastic waist feature and elastic leg features, more preferably an absorbent assembly such as a topsheet and an absorbent core to contain body exudates, and most preferably apertures and vents in at least the side panels to enhance the breathability of the pull-on garment.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). A "unitary" pull-on garment refers to pull-on garments which are formed of separate parts united together to form a coordinated entity, but the side panels are not separate elements joined to a separate chassis in that the side panels are formed by at least one layer which also forms the central panel or chassis of the garment (i.e., the garment does not require separately manipulative panels such as a separate chassis and separate side panels). The pull-on garment is also preferably "absorbent" to absorb and contain the various exudates discharged from the body. A preferred embodiment of the pull-on garment of the present invention is the unitary disposable absorbent pull-on garment, pull-on diaper 20, shown in FIG. 1. As used herein, the term "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like.

Figure 1:
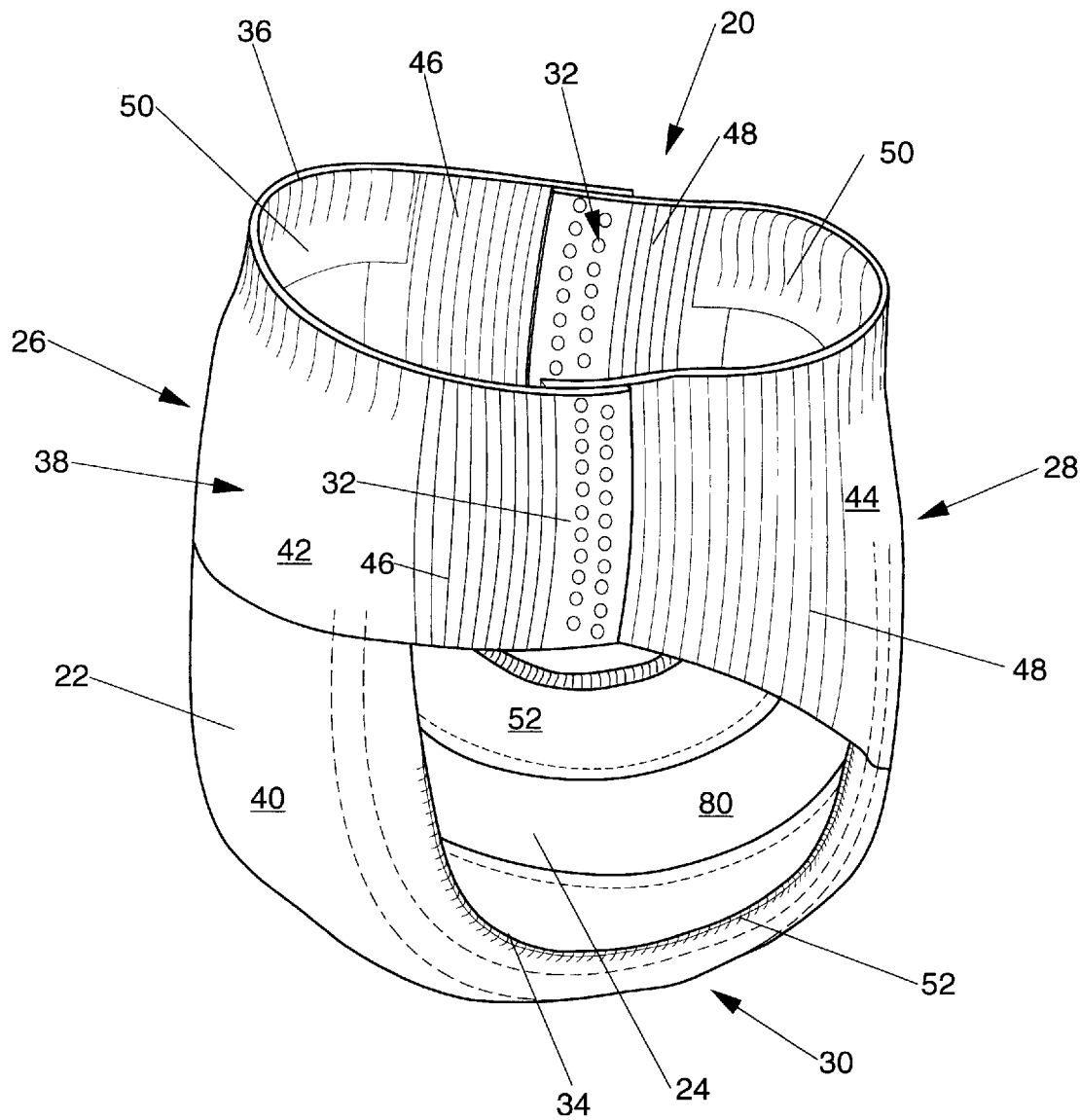
FIG. 1 is a perspective view of the disposable pull-on garment of the present invention in a typical in use configuration.

FIG. 1 is a perspective view of the pull-on diaper 20 of the present invention. The pull-on diaper 20 has an outer surface 22, an inner surface 24 opposed to the outer surface 22, a front region 26, a back region 28, a crotch region 30, and seams 32 which join together the front region 26 and the back region 28 to form leg openings 34 and a waist opening 36. A continuous belt 38 is formed about the waist opening 36. The continuous belt 38 acts to dynamically create fitment forces and to distribute the forces dynamically generated during wear. The pull-on diaper 20 thus preferably comprises a chassis layer 40; a first belt layer 42; a second belt layer 44; an elastically extensible stretch laminate positioned in each side panel of the front region 26, front stretch laminates 46; an elastically extensible stretch laminate positioned in each side panel of the back region 28, back stretch laminates 48; and an elastic waist feature 50 positioned in both the front region 26 and the back region 28. The pull-on diaper 20 additionally comprises elastic leg features 52. (In an alternative embodiment, apertures or vents (not shown) are most preferably provided in at least the side panels of the pull-on diaper 20 to provide breathability and ventilation.) Because the first belt layer 42 and the second belt layer 44 (the belt layers) are preferably nonwoven webs having the appearance of cloth and the chassis layer 40 is preferably a plastic film, the pull-on diaper 20 has a unique aesthetic feature in that it is perceived by caregivers and wearers to have a garment-like comfort and feel in the waist regions while having a perceived containment benefit in the crotch region.

Figure 1A:
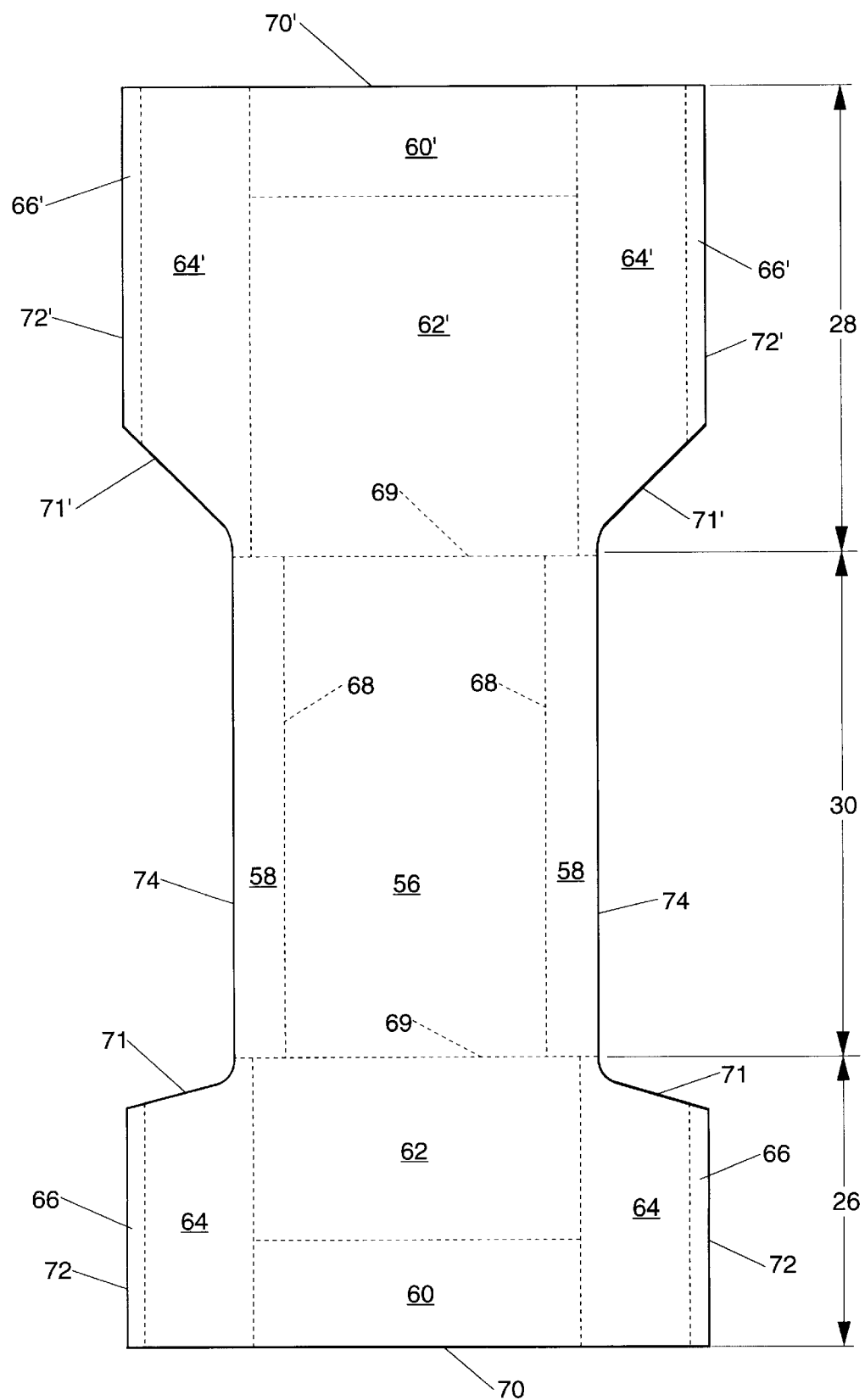
FIG. 1A is a simplified plan view of the pull-on garment of the present invention in its flat uncontracted condition showing the various panels or zones of the garment.

FIG. 1A shows a simplified plan view of the pull-on diaper 20 of FIG. 1 in its flat-out, uncontracted state depicting the various panels and their positioning with respect to each other. The term "panel" is used herein to denote an area or element of the pull-on diaper or the belt. (While a panel is typically a distinct area or element, a panel may coincide (functionally correspond) somewhat with an adjacent panel.) The pull-on diaper 20 has a crotch region 30 comprising a main panel 56 and a pair of leg flap panels 58; a front region 26 comprising a central panel comprising a waistband panel 60 and a medial panel 62, side panels 64, and seam panels 66; and a back region 28 comprising a central panel comprising a waistband panel 60 and a medial panel 62', side panels 64', and seam panels 66'. The crotch region 30 is the portion of the pull-on diaper 20 from which the continuous belt (the other panels) emanates. The absorbent core is generally positioned within the main panel 56 since exudates are typically discharged in this region although the absorbent core will typically extend into the medial panels 62 and 62' of the belt. A leg flap panel 58 extends generally laterally outwardly from and along each side edge 68 of the main panel 56. Each leg flap panel 58 generally forms at least a portion of the elastic leg feature. The continuous belt (the front region 26 and the back region 28) extends generally longitudinally outwardly from and along each lateral edge 69 of the crotch region 30 (the main panel 56 and the leg flap panel 58). In the front region 26, the medial panel 62 of the central panel extends generally longitudinally outwardly from and along the lateral edge 69 of the crotch region 30. The waistband panel 60 extends generally longitudinally outwardly from and along the medial panel 62. The side panels 64 each extend generally laterally outwardly from and along the central panel. The seam panels 66 each extend generally laterally outwardly from and along the respective side panel 64. In the back region 28, the medial panel 62' of the central panel extends generally longitudinally outwardly from and along the other lateral edge 69 of the crotch region 30. The waistband panel 60' extends generally longitudinally outwardly from and along the medial panel 62'. The side panels 64' each extend generally laterally outwardly from and along the central panel. The seam panels 66 each extend generally laterally outwardly from and along the respective side panel 64'. The front region 26, in addition to its panels, also has an end edge 70, leg edges 71, and side edges 72. The back region 28, in addition to its panels, also has an end edge 70', leg edges 71', and side edges 72'. The crotch region 30 has leg edges 74.

Figure 2:
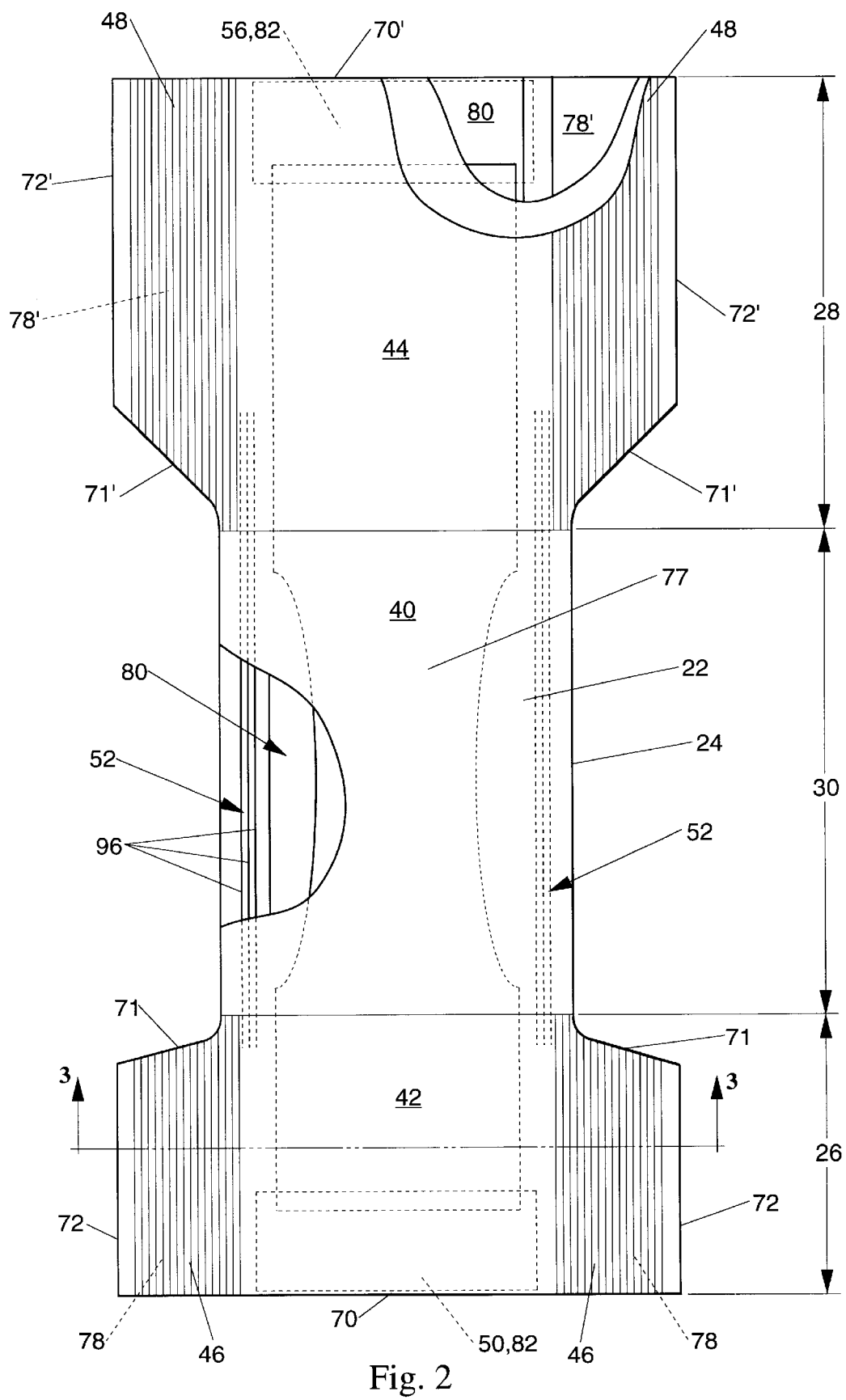
FIG. 2 is a plan view of the pull-on garment of the present invention in its flat uncontracted condition showing the outer surface and having portions cut away to reveal underlying structure.

FIG. 2 is a partially cut-away plan view of the pull-on diaper 20 of FIG. 1 in its flat-out, uncontracted state (i.e., with elastic induced contraction pulled out except in the side panels 64 wherein the stretch laminates (front stretch laminates 46 and back stretch laminates 48) are left in their relaxed condition) with the outer surface 22 facing the viewer, prior to the front region 26 and the back region 28 being joined together by the seams 32. The outer surface 22 of the pull-on diaper 20 comprises that portion which is positioned away from the wearers body during use. In the embodiment shown, the outer surface 22 of the pull-on diaper 20 comprises the first belt layer 42 in the front region 26, the second belt layer 44 in the back region 28, and the chassis layer 40 in the crotch region 30. (The inner surface 24 of the diaper is opposed to the outer surface 22 and comprises that portion of the diaper which is positioned adjacent to the wearer's body during use.)

In the embodiment shown in FIG. 2, the chassis layer 40 preferably comprises a continuous sheet or web which defines the front region 26, the back region 28, and the crotch region 30. Thus, the chassis layer 40 is the primary stratum or layer of the pull-on diaper. (As used herein, the term "layer" does not necessarily limit the element to a single strata of material in that a layer may actually comprise laminates or combinations of sheets or webs of the requisite type of materials.) The chassis layer 40 has an inner surface 76 (not shown in FIG. 2) and an outer surface 77. The inner surface 76 and outer surface 77 of the chassis layer 40 correspond in their orientation with the inner surface 24 and the outer surface 22 of the pull-on diaper 20. Since the chassis layer 40 preferably defines the front region 26, the back region 28, and the crotch region 30, the chassis layer 40 also has corresponding regions and panels as previously defined. (For simplicity, these regions and panels are denoted in the drawings by the same reference numerals as the corresponding pull-on diaper regions and panels as shown in FIG. 1A.) The first belt layer 42 is positioned on the outer surface 77 of the chassis layer 40 in the front region 26 and extends continuously laterally across the front region 26 from one side edge 72 to the other side edge 72 and longitudinally from the end edge 70 to at least the leg edges 71. The first belt layer 42 is preferably joined to the chassis layer 40. The second belt layer 44 is positioned on the outer surface 77 of the chassis layer 40 in the back region 28 and extends continuously laterally across the back region 28 from one side edge 72' to the other side edge 72' and from the end edge 70' to at least the leg edges 71'. The second belt layer 44 is preferably joined to the chassis layer 40. Thus, each belt layer in combination with the chassis layer 40 forms a continuous belt (as shown in FIG. 1) about the waist of the wearer. As will be detailed below, this belt has various elastic extension properties in various zones to enhance the fit and containment of the pull-on diaper 20.

Elastically extensible stretch laminates (front stretch laminates 46 and back stretch laminates 48) are formed in each side panel of both the front region 26 and the back region 28. Each front stretch laminate 46 at least comprises the portion of the first belt layer 42 in the side panel and an elastic panel member 78 joined thereto, and, in this particular embodiment, the portion of the chassis layer 40 forming the side panel. Preferably, the elastic panel member 78 is positioned between the chassis layer 40 and the first belt layer 42, and more preferably extends longitudinally from the end edge 70, most preferably to the leg edge 71. Each rear stretch laminate 48 at least comprises the portion of the second belt layer 44 in each side panel and an elastic panel member 78' joined thereto, and, in this particular embodiment, the portion of the chassis layer 40 forming the side panel. Preferably, the elastic panel member 78' is positioned between the chassis layer 40 and the second belt layer 44, and more preferably extends longitudinally from the end edge 70', most preferably to the leg edge 71'. In the pull-on diaper embodiment shown in FIG. 2, each stretch laminate preferably further comprises a portion of the topsheet 80 (the barrier layer) in the side panel. Each stretch laminate is mechanically stretched or drawn (designated by the strain lines) to allow the stretch laminate to be elastically extensible in at least the lateral direction. (The lateral direction (x direction or width) is defined as the direction parallel to the lateral centerline of the pull-on diaper, the longitudinal direction (y direction or length) is defined as the direction parallel to the longitudinal centerline; and the axial direction (z direction or thickness) is defined as the direction extending through the thickness of the pull-on diaper.)

An elastic waist feature 50 is provided in the waistband panel of the front region 26, the back region 28, or preferably both the front region 26 and the back region 28. The elastic waist feature 50 provides an elastically extensible member, preferably a gathered elastically contractible member, to dynamically fit and conform to the waist of the wearer in the central panels. In the embodiment shown, the elastic waist feature 50 preferably comprises a unitary waistcap/waistband 82 operatively joined in the waistband panel in an elastically contractible condition, preferably to the primary layer of the topsheet 80. The unitary waistcap/waistband 82 acts as a barrier to the leakage of exudates out of the waist opening of the pull-on diaper 20 as well as a contractible waistband to provide fit of the pull-on diaper 20 about the waist of the wearer. In the most preferred embodiments, the unitary waistcap/waistband is also breathable to allow venting of water vapor out of the pull-on diaper adjacent the waist opening.

The pull-on diaper 20 is also provided with elastic leg features 52 to improve fit at the legs in the crotch region 30. The pull-on diaper 20 additionally comprises a topsheet 80 and an absorbent core 84 positioned between the topsheet 80 and the chassis layer 40 to provide an absorbent assembly that cooperates with the continuous belt to contain discharged exudates. Apertures or vents (not shown) may also be positioned in the side panels to provide breathability or ventilation.

Figure 3:
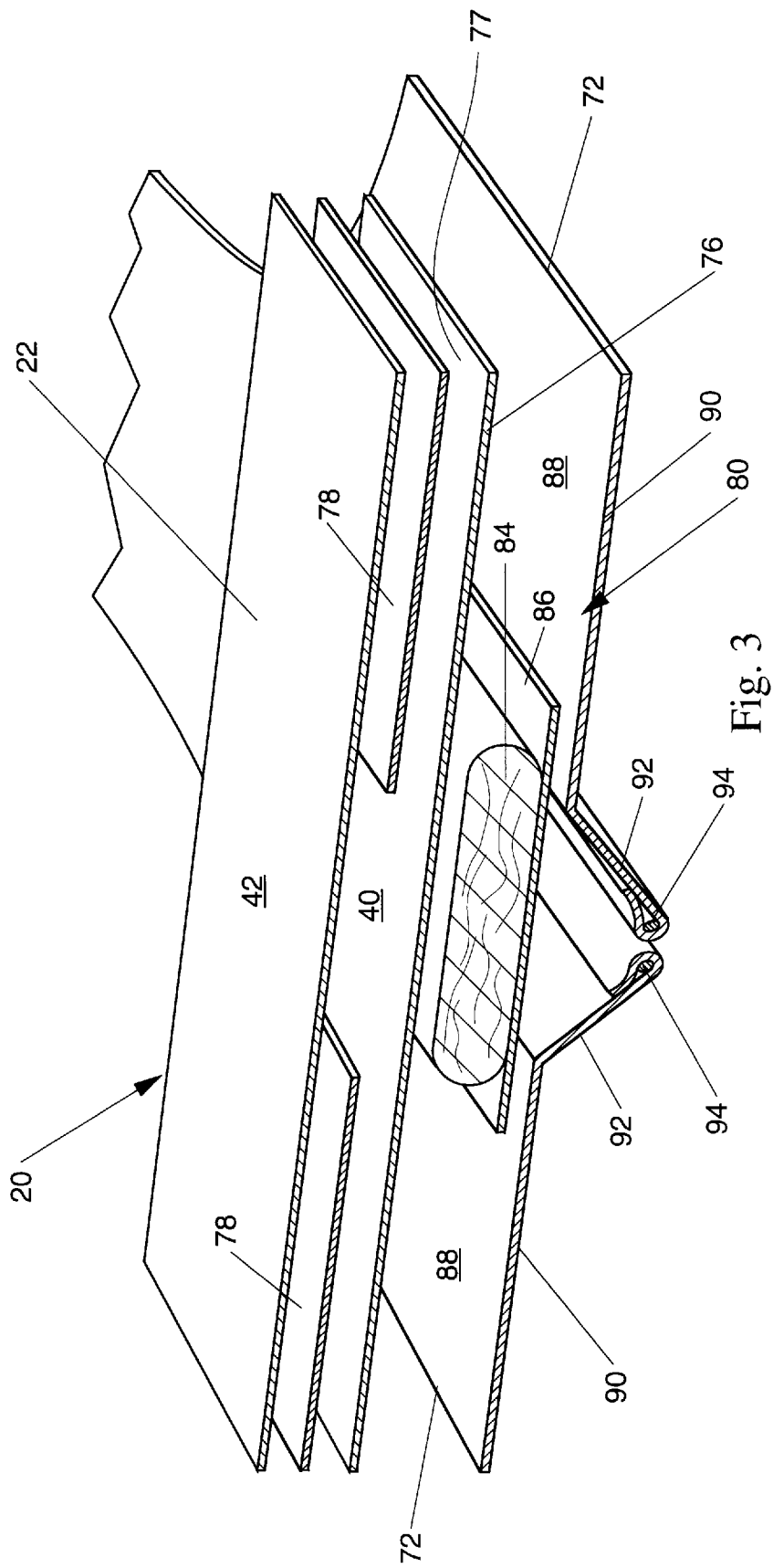
FIG. 3 is a fragmentary view of the pull-on garment shown in FIG. 2 taken along section line 3—3 of FIG. 2.

FIG. 3 is a cross-sectional perspective view of the pull-on diaper 20 of the present invention taken along line 3—3 of FIG. 2 in the front region 26. The chassis layer 40 is shown to form the primary strata or layer of the pull-on diaper 20 and has an inner surface 76 and an outer surface 77. The first belt layer 42 is positioned on the outer surface 77 of the chassis layer 40 to form the outer surface 22 of the pull-on diaper 20 in the front region 26. The elastic panel members 78 are preferably positioned between the first belt layer 42 and the chassis layer 40. The topsheet 80 is positioned on and joined to the inner surface 76 of the chassis layer 40. The topsheet 80 preferably comprises a liquid pervious primary layer 86 and two barrier layers 88. The barrier layers 88 extend laterally outwardly from the primary layer 86 to the side edges 72. Each barrier layer 88 comprises a flap portion 90 and a stand-up portion 92. The stand-up portion 92 is not attached to the primary layer 86 to allow the gathering forces of the elastic spacing member(s) 94 to cause the stand-up portion 92 to stand up away from the surface of the primary layer 86 to form a barrier or wall in use. The flap portion 90 extends laterally outwardly from the stand-up portion 92 (the proximal edge) to the side edge 72. The absorbent core 84 is preferably positioned between the primary layer 86 and the chassis layer 40. The construction of the back region 28 is preferably identical to the construction of the front region 26.

Figure 4:
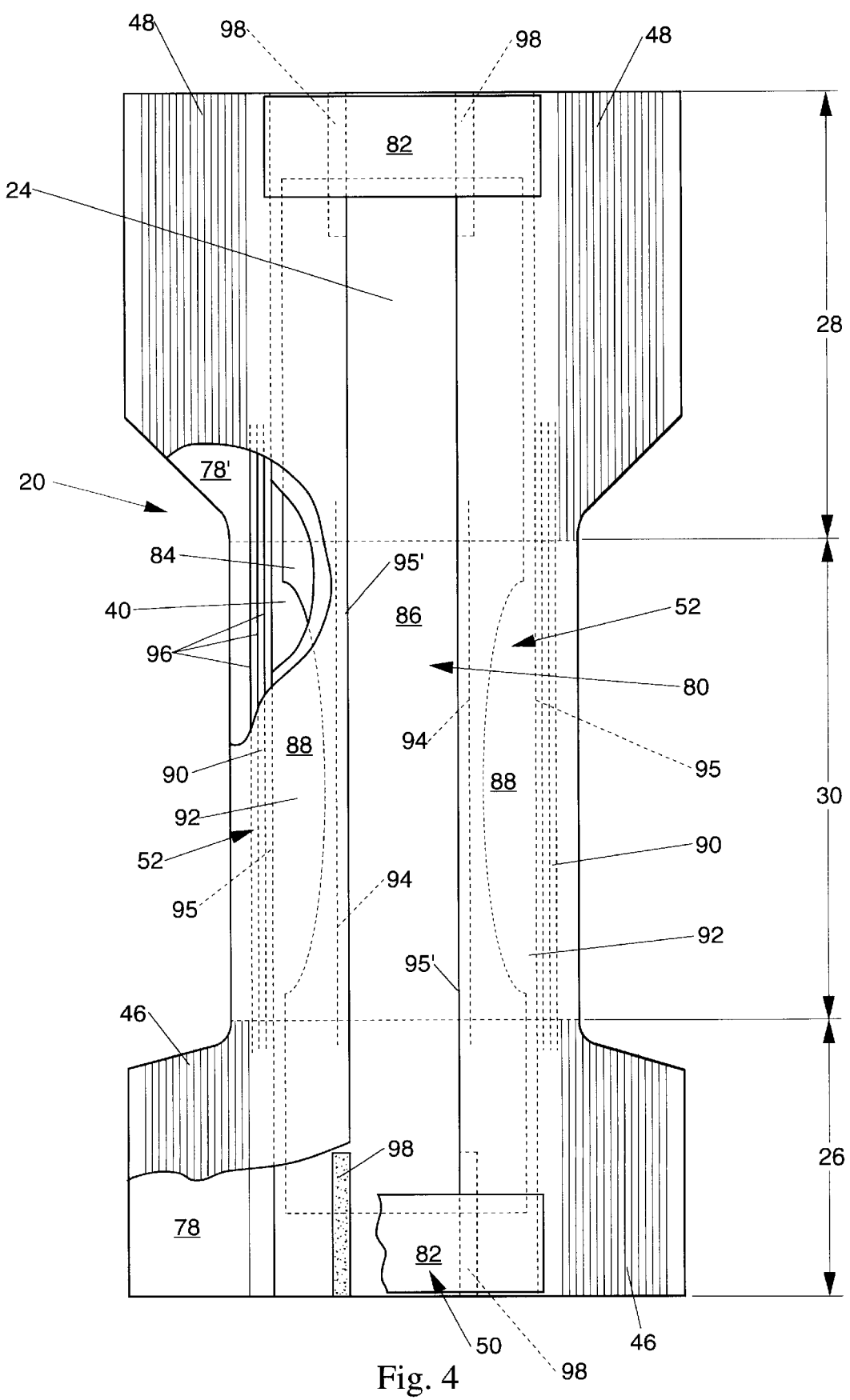
FIG. 4 is a plan view of the pull-on garment of the present invention in its flat uncontracted condition showing the inner surface and having portions cut away to reveal underlying structure.

FIG. 4 is a partially cut-away plan view of the pull-on diaper 20 of the present invention in its flat-out, uncontracted state (i.e., with elastic induced contraction pulled out except in the side panels wherein the stretch laminates are left in their relaxed condition) with the inner surface 24 of the pull-on diaper 20 facing the viewer, prior to the front region 26 and the back region 28 being joined together by the seams. In order to provide the necessary absorbency to contain body exudates, the pull-on diaper 20 comprises a liquid pervious topsheet 80 and an absorbent core 84 positioned between the topsheet 80 and the chassis layer 40. In the embodiment shown in FIG. 4, the topsheet 80 preferably comprises three distinct layers joined together. A liquid pervious primary layer 86 is positioned over the absorbent core 84 to rapidly absorb liquids into the product. Barrier layers 88 are joined to the primary layer 86 and are preferably drawable, more preferably hydrophobic, to allow the side panels to be mechanically stretched without ripping or tearing while providing barrier cuffs along the sides of the pull-on diaper 20. The barrier layers 88 have a flap portion 90 and a channel or stand-up portion 92 to provide the various components of the elastic leg features 52. The elastic leg features 52 preferably comprise a gasketing cuff and a barrier cuff. The gasketing cuff is preferably formed by one or more elastic leg members 96 operatively joined to the chassis layer 40, the barrier layer 88, or both, preferably between the chassis layer 40 and the flap portion 90 of the barrier layer 88 in the leg flap panel of the crotch region 30. The barrier cuff is preferably formed by a flap (the stand-up portion 92 of the barrier layer 88), closing means 98 for securing the longitudinal ends of the stand-up portion 92 to the primary layer 86, and an elastic spacing member 94 operatively joined to the stand-up portion 92.

In the construction of the pull-on diapers of the present invention as is shown in FIG. 1, a continuous belt 38 is formed about the waist opening 36. This belt 38 acts to dynamically create fitment forces in the pull-on diaper when positioned on the wearer, to maintain the pull-on diaper on the wearer even when loaded with body exudates thus keeping the absorbent core in close proximity to the wearer, and to distribute the forces dynamically generated during wear about the waist thereby providing supplemental support for the absorbent core without binding or bunching the absorbent core in the medial panel of the pull-on diaper. The belt is designed to be elastically extensible in certain segments and at least elastically extensible, preferably elastically contractible, in other segments about the waist opening; to be elastically extensible about a portion of the leg opening; and to not be gathered or bunched in the medial panel where the absorbent core is located. The elastic extensibility of the belt also has a "force/extension wall" beyond which the belt will not elastically extend in order to allow the pull-on diaper to be more easily applied since the diaper will not stretch excessively thereby allowing the product to slide more easily over the buttocks. This "force/extension wall" is especially important for small children who self apply the product and would be unable to completely pull and position a fully stretchable product over their buttocks. The belt also manages wearing stresses better with the belt webs encircling the absorbent core. The resultant diaper is less bulky in its fit about the waist of the wearer. The lack of gathering or contraction in the belt over the absorbent core in conjunction with the continuity of the belt across the absorbent core also provides improved fit by providing a continuous normal force based on the hoop stresses generated in the belt which tends to press the absorbent core against the body during wear. Thus, the absorbent core is maintained in a closer, more comfortable, and less gapping way than those diapers which provide elastic contraction or gathering over the area of the absorbent core or those that do not provide a belt to concentrate within the span and distribute across the span the hoop stresses about the area of the absorbent core.

As shown in FIG. 1A, the belt 38, in both the front region 26 and the back region 28 respectively, comprises a central panel comprising a waistband panel 60 and 60' and a medial panel 62 and 62', a side panel 64 and 64' on each side of the central panel, and a seam panel 66 and 66' at each side panel 64 and 64'. The side panels are elastically extensible to provide fit within the sides of the pull-on diaper. The waistband panel is elastically extensible, preferably elastically contractible or gathered, to better fit the pull-on diaper in the central part of the waist opening. The medial panel is not gathered in order to maintain the integrity of the absorbent core during use. Although the medial panel may be elastically extensible (but not gathered) as discussed herein, in the embodiments shown in FIGS. 1–4, the medial panel is preferably not extensible. The continuous belt 38 may be formed from a number of different materials and layers as defined below. The belt 38 comprises at least a first belt layer 42 and a second belt layer 44 joined together on each side at the seam panels 66 and 66'. In the embodiment shown in FIGS. 1–4, the belt 38 preferably comprises a portion of the chassis layer 40, the belt layers (the first belt layer 42 in the front region 26 and the second belt layer 44 in the back region 28), stretch laminates (front stretch laminates 46 and back stretch laminates 48) in the side panels, and an elastic waist feature 50 in each waistband panel, preferably comprising a unitary waistcap/waistband 82 operatively joined in an elastically contractible condition to gather the belt 38 in the waistband panels 60 and 60'.

In preferred embodiments of the present invention, the chassis layer 40 generally determines the overall shape of the pull-on diaper 20. The chassis layer 40 acts as the main structural layer of the pull-on diaper to which other features may be added or joined. The chassis layer is thus positioned in all or most of the surface area of the pull-on diaper, although in certain embodiments certain portions of the chassis layer may be apertured, cut-out or removed ("windowed") to enhance stretchability and/or breathability of the pull-on diaper or features of the pull-on diaper in that area.

The chassis layer thus preferably comprises a continuous sheet or web which does not have "joints" or seams such that forces are distributively transmitted through the entire layer. As previously discussed herein, the continuous sheet or web of the chassis layer can comprise a single web of material or a laminate of several continuous webs or layers of different materials. The chassis layer forms a part of the continuous "belt" that provides the necessary force/extension properties to hold the diaper on the wearer while expanding to allow the pull-on diaper to be put on easily. The chassis layer may form the outer surface, the inner surface, or portions of either or both, or may be entirely positioned in the interior of the pull-on diaper. In the embodiment of the present invention shown in FIGS. 1–4, the chassis layer preferably forms the outer surface of the pull-on diaper in the crotch region to provide the unique aesthetics of the pull-on diaper.

Since at least a portion of the chassis layer 40 is subjected to mechanical stretching in order to provide the stretch laminates in the side panels, it is preferably elongatable, more preferably drawable (but not necessarily elastomeric), so that the chassis layer will, upon mechanical stretching, be at least to a degree permanently elongated such that it will not fully return to its original undistorted configuration. The chassis layer may thus comprise any of the materials known for use in absorbent articles such as woven or nonwoven webs; polymeric films such as thermoplastic films of polyethylene, polypropylene, or blends thereof; laminates of such materials; or composite materials. In preferred embodiments, the chassis layer can be subjected to mechanical stretching with minimal or no rupturing or tearing. Therefore, the chassis layer 40 is preferably a polymeric film.

Because the chassis layer 40 is preferably a polymeric film, it is also generally impervious to liquids (e.g., urine) so that it may also serve as the component which prevents exudates absorbed and contained in the absorbent core from wetting garments which contact the pull-on diaper such as bed sheets and undergarments (i.e., it acts as the traditional diaper backsheet). If the chassis layer is not liquid impervious, typically an additional layer such as a traditional backsheet should be used behind the absorbent core. The chassis layer may also be breathable (pervious to air or water vapor) if desired. In particular, since the belt layers, and preferably the barrier layers, are each drawable nonwoven webs to strengthen the stretch laminates to carry the forces and since there is no need for a high lateral tensile strength material in the crotch region, the chassis layer can alternatively comprise breathable materials that are microporous and that are, typically, lower in strength and elongation. An example of such a film is that manufactured by Exxon Chemical Company under the tradename EXXAIRE. Exemplary films for use as the chassis layer of the present invention having relatively good drawability but that are not breathable include polymeric films manufactured by Clopay Corporation of Cincinnati, Ohio under the designation Clopay 1401, or films available from Tredegar of Terre Haute, Ind., under the designation X-8323 or X-9954.

The size of the chassis layer is dictated by the size of the wearer the pull-on diaper is designed to fit. In a preferred embodiment, the chassis layer has a modified hourglass shape to better fit the wearer. In a preferred embodiment designed to fit large toddlers (about 9 kg to about 15.4 kg), the chassis layer 40 is preferably about 483 mm (about 19 inches) long by about 234 mm (about 9¼ inches) wide in the front region and the back region and about 165 mm (about 6½ inches) wide in the crotch region. The central panel is 135 mm (about 5¼ inches) wide, the side panels are about 41 mm (about 1⅝ inches) wide, the activated portion of the side panels is about 32 mm (about 1¼ inches) wide, and the seam panels are about 8.5 mm (about 5/16 inch) wide. (The actual area of overlap of the seam panels is about 11 mm in the preferred embodiments shown herein.) The front region is about 114 mm (about 4½ inches) long, the back region is about 165 mm (about 6½ inches) long, and the crotch region is about 220 mm (about 8⅝ inches) long.

The belt layers (first belt layer 42 and second belt layer 44) act, preferably in conjunction with the chassis layer 40 and other components, to form the continuous belt 38 about the waist opening 36 of the pull-on diaper 20. The belt layers each thus preferably comprise a continuous sheet or web that does not have "joints" or seams such that forces are distributively transmitted through the entire belt layer. (The continuous sheet or web of each belt layer can comprise a single web of material or a laminate of several continuous webs or layers of different materials.) The materials of the belt layers also preferably provide strength to the stretch laminates in the side panels to laminate the materials together and permit mechanical stretching without undue ripping, tearing or shredding of the materials.

In the embodiment shown in FIGS. 1–4, the belt layers are preferably positioned on and joined to the outer surface of the chassis layer so as to form a portion of the outer surface of the pull-on diaper. However, the belt layers may be positioned on the inner surface of the chassis layer, and, in some embodiments, may form a portion of the inner surface of the pull-on diaper. Some of these alternative embodiments are shown and described hereinafter. The belt layers are joined to the chassis layer by attachment means (not shown) at least in the side panel. Suitable attachment means are described herein. The belt layers extend laterally continuously across the respective waist region (front region or back region) of the pull-on diaper to provide the continuous belt 38 described herein and extend longitudinally from the end edge to about the crotch region. Alternatively, the belt layers may longitudinally extend into the crotch region to provide more of the pull-on diaper with a garment-like feel. While it is preferred that the first belt layer and the second belt layer extend longitudinally inward so as to leave a gap between them in the crotch region to provide the aesthetic benefit described herein, they can be overlapped, if desired, to provide an overall cloth-like appearance and feel.

Since the belt layers are subjected to mechanical stretching in the side panels, the belt layers are preferably elongatable, more preferably drawable (but not necessarily elastomeric), without undue or, preferably any, tearing or ripping. Further, because the belt layers are preferably positioned on the outer surface of the pull-on diaper, the belt layers are preferably also compliant, soft feeling, and non-irritating to the wearer's skin to give the diaper the feel and comfort of a cloth garment. Suitable belt layers can be manufactured from a wide range of materials such as plastic films; apertured plastic films; woven or nonwoven webs of natural fibers (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. Preferably, the belt layers comprise a nonwoven web of synthetic fibers.

In typical nonwoven webs, localized rupturing of the web is caused in certain regions as the web is passed between the mechanical stretching rolls. This rupturing may be attributed to a lack of necessary extensibility of the nonwoven web or to a lack of drawability of the individual fibers. The preferred nonwoven webs of the present invention exhibit high extensibility and preferably allow the individual fiber to be drawn such that the bonds between the fibers are not substantially ruptured or broken. Thus, the belt layers are most preferably highly extensible nonwoven webs that will generally more uniformly elongate with minimal localized strain tearing occurring compared to typical nonwoven webs consisting of less drawable fibers. Examples of such nonwoven webs include spunbonded webs of polyethylene or polyethylene-blend fibers. More preferably, the belt layers are made from a spunbonded web of fibers made of polyethylene, polyethylene polymer blends, or polyethylene/polypropylene polymer blends. Exemplary spunbonded nonwoven webs of polyethylene fibers for use as the belt layers are available as #87257 manufactured by Polybond Co. of Waynesboro, Va.; as COROLIND 17184 manufactured by Corovin of Peine, Germany; or as Fiberweb E1004204 manufactured by Fiberweb of Simpsonville, S.C..

The belt 38 is elastically extensible in the side panels 64 and 64' to provide a more comfortable and contouring fit by initially conformably fitting the pull-on diaper to the wearer and sustaining this fit throughout the time of wear well past when it has been loaded with exudates by distributing forces along both the waist and legs since the sides of the pull-on diaper can expand and contract. The side panels are extensible in at least one direction, preferably in a direction having a vector component in the lateral direction, more preferably in the lateral direction, to provide better fit. It should be noted, however, that the side panels may be extensible in any other direction or in more than one direction. In addition, the side panels may have one or more discrete zones of extensibility.

The elastic extensibility in the side panels may be provided by a number of different materials and configurations. Various components of the belt (e.g., the belt layers or the chassis layer) may comprise conventional elastic materials or the side panels of the belt may be constructed from a number of different elastic laminate structures. For example, the side panels of the belt can comprise an elastic material operatively joined to one or more inelastic components (belt layer or chassis layer or both) in an elastically contractible condition such as is described in U.S. Pat. No. 3,860,003 entitled "Contractable Side Portions For A Disposable Diaper" issued to Buell on Jan. 14, 1975, which is incorporated herein by reference. Alternatively, the side panels can comprise a structural elastic-like film (SELF) web such as described in WO 95/03765, "Web Materials Exhibiting Elastic-like Behavior", The Procter & Gamble Company, published Feb. 9, 1995, which is incorporated herein by reference. While the side panels of the belt may be constructed from a number of different extensible or elastic materials as are known in the art, one or more, and preferably each, of the side panels of the belt are constructed of a stretch laminate.

The stretch laminates (front stretch laminates 46 and back stretch laminates 48) are unitary elements of the pull-on diaper (i.e., they are not separately manipulative elements secured to the pull-on diaper, but rather are formed from and are extensions of one or more of the various layers (at least the belt layer, preferably also the chassis layer) of the pull-on diaper.) In a preferred embodiment, each stretch laminate is formed by a portion of the chassis layer, a portion of the respective belt layer, an elastic panel member positioned between the chassis layer and the belt layer, and a portion of the barrier layer.

Figure 12:
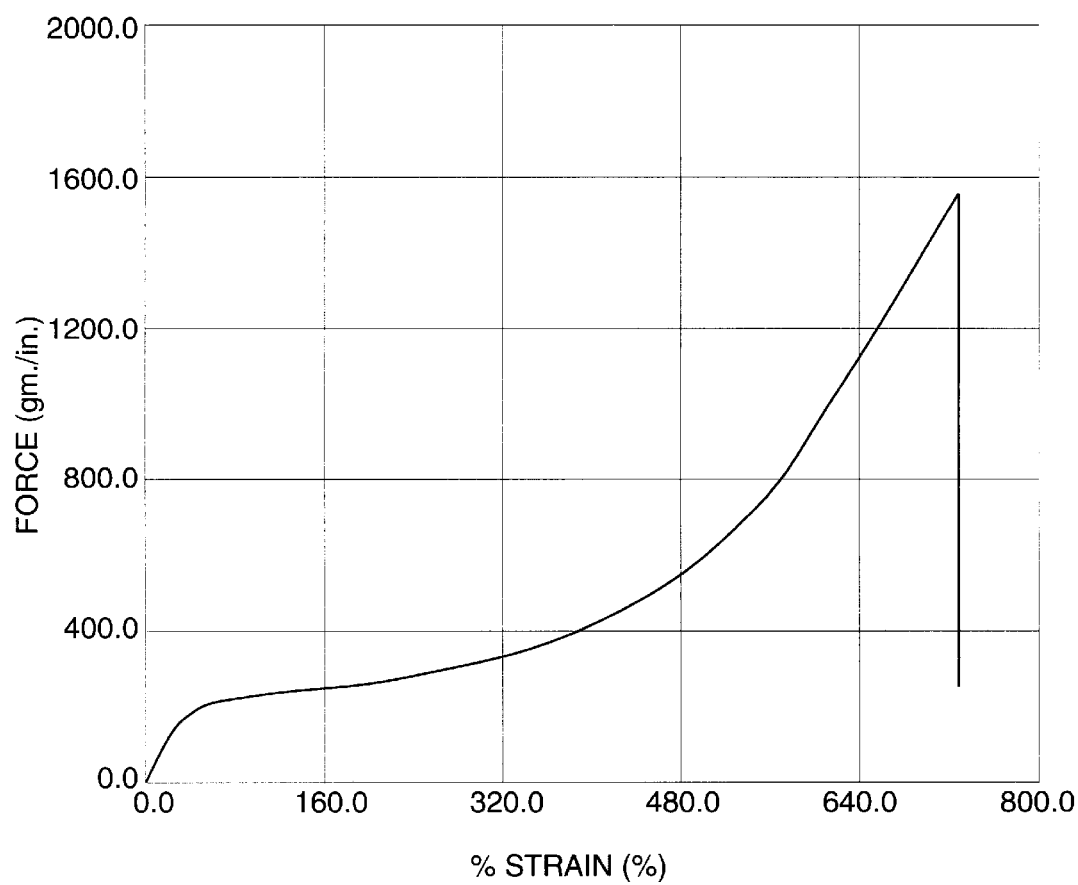
FIG. 12 is a graph of the stress/strain curve in grams per 1 inch wide sample of a particularly preferred elastomeric material for use as the elastic panel member in the stretch laminates of the present invention.

In a preferred embodiment of the present invention, an elastic panel member 78 is operatively joined in the side panel, preferably between the chassis layer and the belt layers, to allow the stretch laminates to be elastically extensible in at least the lateral direction. As used herein, the term "elastically extensible" means a segment or portion that will elongate in at least one direction (preferably the lateral direction for the side panel) when tensional forces (typically lateral tensional forces for the side panel) are applied, and will return to about its previous size and configuration when the tensional forces are removed. Elastomeric materials which have been found to be especially suitable for use as the elastic panel members (especially for zero strain stretch laminates) are styrenic block copolymer based elastic films, preferably with a thickness is of 0.05 mm–0.064 mm (0.002 in–0.0025 in), such as are made by Clopay Corporation of Cincinnati, Ohio under the designation PA18-2870; or Exxon 500 series elastic films from Exxon Chemical of Baytown, Tex. A stress/strain (force/extension) graph of the P18-2870 elastomeric material described above is shown in FIG. 12. The stress/strain graph shows the typical shape of the force curve in grams per 1 inch wide sample when subjected to an applied strain or extension at a rate of 50.8 cm/min (20 in/min) at about 23° C. (room temperature). Other suitable elastomeric materials for use as the elastic panel members include "live" synthetic or natural rubber, other synthetic or natural rubber foams, elastomeric films (including heat shrinkable elastomeric films), elastomeric woven or nonwoven webs, scrims, elastomeric composites, or the like.

In an especially preferred embodiment, the elastic panel members are operatively joined in the side panel by securing them to the chassis layer, the belt layer, or both while in a substantially untensioned (zero strain) condition. At least a portion of the resultant composite stretch laminate containing the elastic panel member is then subjected to mechanical stretching sufficient to permanently elongate the non-elastic components (the chassis layer, the barrier layer, and the belt layer) of the stretch laminate. The composite stretch laminate is then allowed to return to its substantially untensioned condition. The side panel is thus formed into a "zero strain" stretch laminate. (Alternatively, the elastic panel member could be operatively joined in a tensioned condition and then subjected to mechanical stretching; although this is not as preferred as a "zero strain" stretch laminate.) As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching. Particularly preferred methods and apparatus used for making stretch laminates utilize meshing corrugated rolls to mechanically stretch the components. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; and U.S. Pat. No. 5,143,679 issued to Weber et al. on Sep. 1, 1992; each of which are incorporated herein by reference.

The elastic panel members can be operatively joined in the stretch laminate to the chassis layer, the belt layers, or both, using either an intermittent bonding configuration or a substantially continuous bonding configuration. As used herein, an "intermittently" bonded laminate web means a laminate web wherein the plies are initially bonded to one another at discrete spaced apart points or a laminate web wherein the plies are substantially unbonded to one another at discrete spaced apart areas. Conversely, a "substantially continuously" bonded laminate web means a laminate web wherein the plies are initially bonded substantially continuously to one another throughout the areas of interface. Because it is preferred that the stretch laminate be bonded over all or a significant portion of the stretch laminate so that the inelastic webs (belt layers, chassis layer, and barrier layers) elongate or draw without causing rupture, and the layers of the stretch laminates are preferably bonded in a configuration that maintains all of the layers of the stretch laminate in relatively close adherence to one another after the incremental mechanical stretching operation, the elastic panel members and the other plies of the stretch laminate are substantially continuously bonded together using an adhesive. In a particularly preferred embodiment, the adhesive selected is applied in a spiral pattern (such as is shown in U.S. Pat. No. 3,911,173 (Sprague, Jr.) and U.S. Pat. No. 4,842,666 (Werenicz)) at a basis weight of about 0.00116 grams/square cm (0.0075 grams/square inch). The spirals have a width of about 1.9 cm (0.75 in) and either are positioned just next to each other or overlap slightly (less than 2 mm). The adhesive is preferably an adhesive such as is available from Findley Adhesives under the designation H2120. Alternatively, the elastic panel member and any other components of the stretch laminates may be intermittently or continuously bonded to one another using heat bonding, pressure bonding, ultrasonic bonding, dynamic mechanical bonding, or any other method as is known in the art.

It has been found that the extension characteristics including the extension forces, extension modulus, and available stretch (extension); and the contractive forces and rate of contraction of the stretch laminates are important considerations in the performance of both the stretch laminates and the pull-on diaper. The extension properties and fitment forces give the applicator and the wearer the overall perceived "stretchiness" during use. They also effect the ability of the applicator to achieve a suitable degree of application stretch (i.e., for a "normally" perceived tensioning of the diaper during application, the total amount of resultant stretch is that desired to achieve/maintain good conformity of fit). A stretch laminate with a relatively high extension modulus/force can cause red marking on the wearer's skin while a relatively low extension modulus/force can cause sagging/slipping on the wearer. Stretch laminates having too little available stretch may not achieve a suitable level of body conformity and may contribute in making the diaper uncomfortable to wear and hard to put on. Stretch laminates with very low contractive forces (or excessive elastic creep, excessive elastic force relaxation, or excessive inelastic "set") may not stay in place on the wearer and may tend to sag/slip on the wearer resulting in poor fit and containment.

Figure 13:
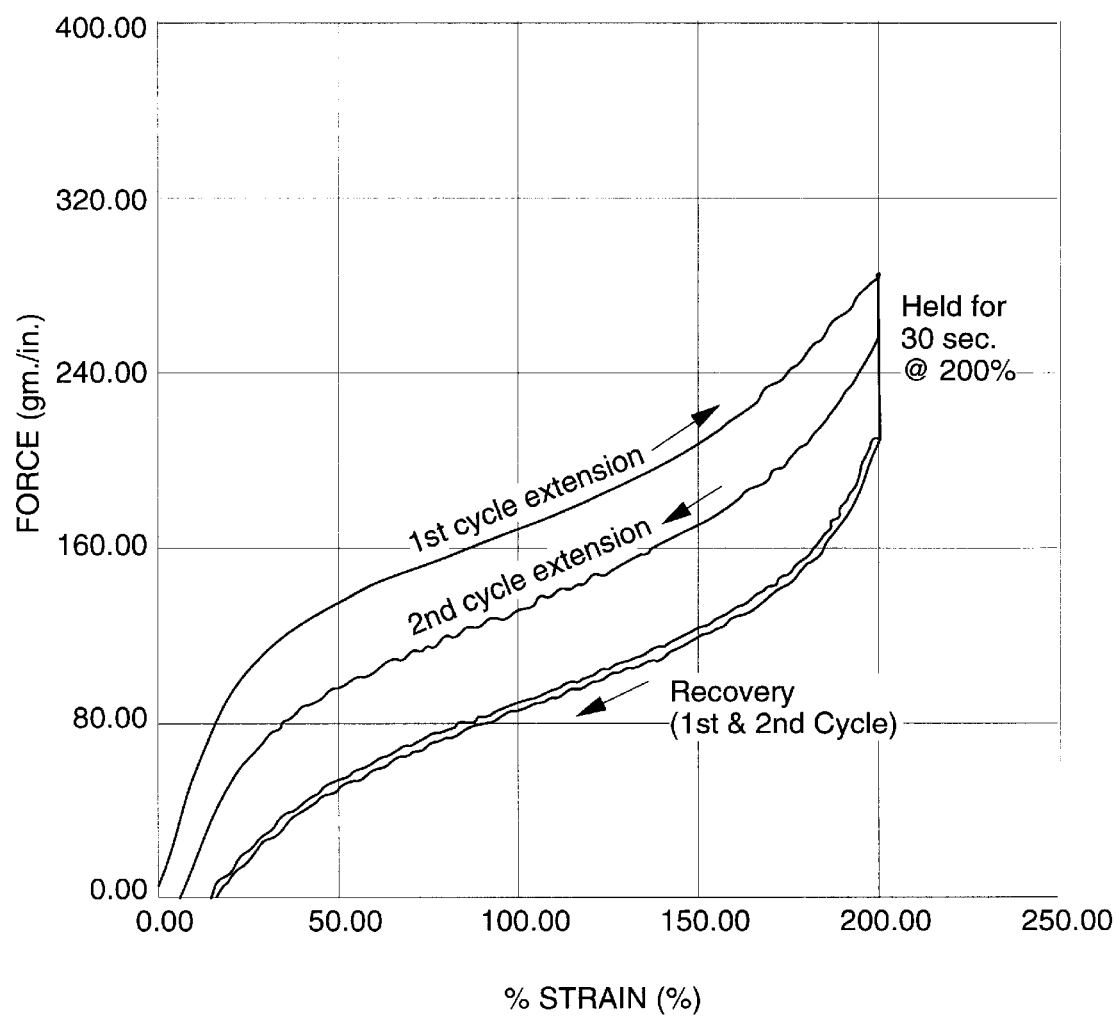
FIG. 13 is a graph of stress/strain, both extension and recovery curves, in grams per 1 inch wide sample of a stretch laminate of the present invention that does not have vents.

For the stretch laminates of the present invention it has been found that the extension characteristics of extension force and extension modulus are preferably within defined ranges. FIG. 13 shows an extension/force response curve for two extension/recovery cycles on a preferred (nonvented) stretch laminate of the present invention. The sample stretch laminate is subjected to an initial pull or extension at a rate of 50.8 cm/min (20 in/min) at about 23° C. and held for 30 seconds at 200% extension. The sample is then allowed to relax at the same rate. The sample is allowed to remain unconstrained for one minute before being subjected to a second pull or extension at the same rate and conditions. The initial pull extension force preferably is greater than or equal to about 100 grams/in at 100% extension. More preferably, the initial pull extension forces are between about 150 to about 225 grams/in, most preferably between about 160 grams/in and 200 grams/in, at 100% extension to best fit the wearer. At 200% extension, the initial pull extension forces are preferably between about 200 grams/in and about 400 grams/in, more preferably between about 240 grams/in and about 320 grams/in. The second cycle recovery forces of the stretch laminates within the wearing ranges (20% to 140% extension) are preferably between about 25 grams/in and about 200 grams/in on recovery, more preferably between about 60 grams/in and about 150 grams/in. These values correspond to the nominal wearing force after extension and recovery.

Figure 14:
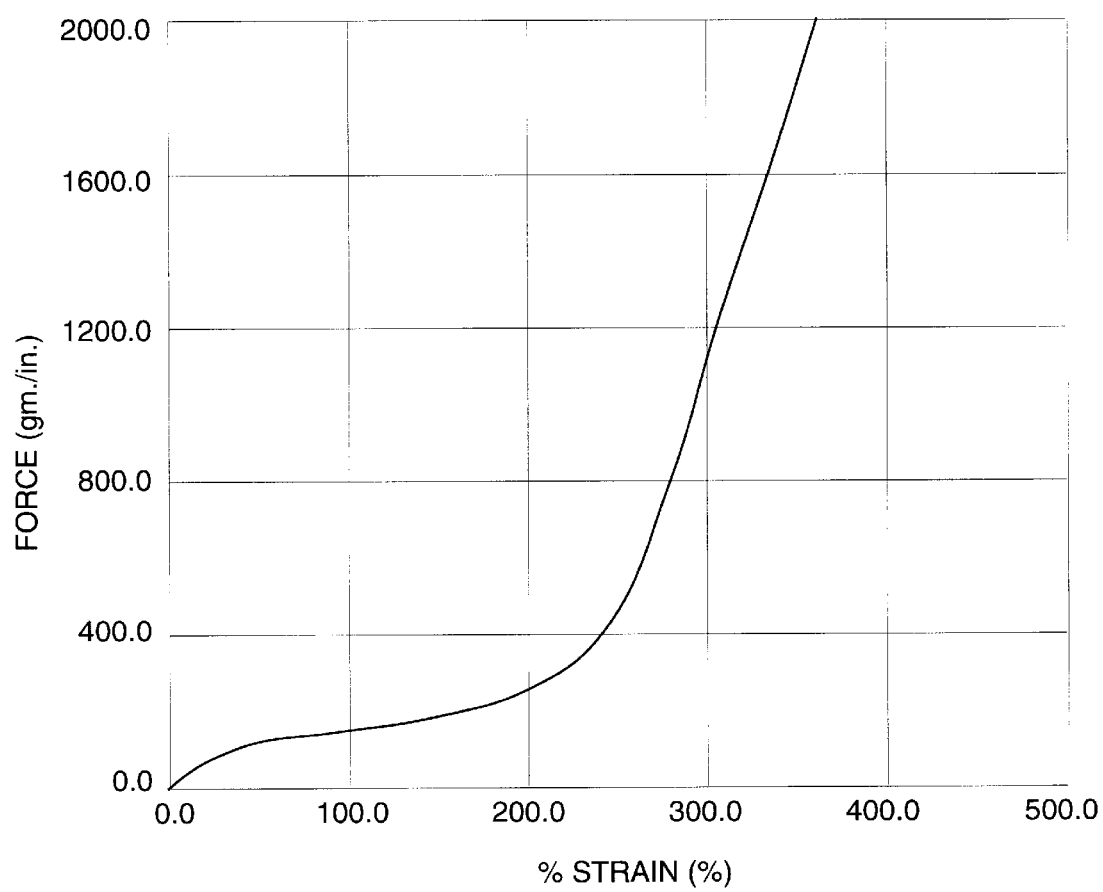
FIG. 14 is a graph of the stress/strain curve in grams per 1 inch wide sample of the stretch laminate of FIG. 13 showing the force wall generated by these stretch laminates.

The force wall is that portion of the extension curve where forces are more rapidly developing with increasing extension. The force wall allows additional pull-on force to be developed without additional excessive stretching of the belt. This results in the garment being easier to put on, especially for self-application. The force wall is achieved at forces greater than 400 grams/in. Thus, for the stretch laminates, an incremental increase in extension of 50% or less beyond the desired maximum design extension produces a force above 400 grams/in. As shown in FIG. 14, the force wall of the stretch laminate is typically achieved at greater than about 200% extension (the desired maximum design extension of this stretch laminate). An increase in extension of 50% from 200% to 250% extension produces a force greater than 400 grams/in.

Available stretch measures the maximum amount of material available in the stretch laminate to reversibly stretch to conform to the wearer's body during wear. Thus, the amount of available stretch relates to the maximum amount of extension that the diaperer has available to fit the diaper to the wearer. In addition, the maximum amount of recoverable extension available for the diaper to comply with the wearer's body. The available stretch is calculated from the equation: ((stretched length−original length)/original length)×100. The minimum amount of available stretch required for a diaper application using the stretch laminates is preferably an available stretch of at least about 75%, preferably at least 100%, with available stretches preferably in the range of 100%–250%, most preferably about 200%.

The continuous belt 38 is also preferably elastically extensible in the central panel, preferably at least in each waistband panel 60 and 60' longitudinally outward from the absorbent core. The elastic extensibility is provided by an elastic waist feature 50. The elastic waist feature 50 provides a member that is elastically extensible, preferably elastically contractible, in at least the lateral direction so as to provide a portion of the continuous belt comprising the stretch laminates of the side panels and the elastic waist features in the waistband panels to dynamically fit and conform to the waist of the wearer so as to provide improved fit. Thus, lines of force along the waist opening are resolved through the upper portions of the stretch laminates in the side panels through the elastic waist feature in the waistband panels. Thus, the elastic waist feature is generally that portion of the belt extending from the end edge to the edge of the absorbent core. The elastic waist feature is preferably elastically contractible in order to gather the waistband panel longitudinally outward from the absorbent core to taper the fit of the garment in the central panel to better fit the wearer.

The elastic waist feature 50 comprises an extension of at least the belt layers (first belt layer 42 or second belt layer 44) and, preferably, one of the other elements of the pull-on diaper such as the chassis layer 40 or the topsheet 80 or any combination of these elements, alone (if one of these layers are extensible or contractible) or with an elastic material joined thereto. The elastic waist feature 50 may be constructed in a number of different configurations including those described herein with regard to the stretch laminates; those elasticized waistbands such as are known in the art and as are described, for example, in U.S. Pat. No. 4,515,595 entitled "Disposable Diapers With Elastically Contractible Waistbands" issued to Kievit & Osterhage on May 7, 1985, and in U.S. Pat. No. 5,151,092 entitled "Absorbent Article With Dynamic Elastic Waist Feature Having A Predisposed Resilient Flexural Hinge" issued to Buell, Clear & Falcone on Sep. 29, 1992; and elasticized waistbands made from a structural elastic-like film (SELF) web as described in the previously referenced WO 95/03765; each of which is incorporated herein by reference.

In a preferred embodiment of the present invention as shown in FIG. 4, the elastic waist feature 50 comprises a unitary waistcap/waistband 82 positioned on the topsheet 80 and operatively joined in an elastically contractible condition with the topsheet 80 to gather the waistband panel 60 or 60' of the pull-on diaper 20. The unitary waistcap/waistband 82 preferably comprises a laminate of a nonwoven coverstock layer, an elastomeric layer, and more preferably a second nonwoven coverstock layer. An example of such a unitary waistcap/waistband for use herein is disclosed in U.S. Pat. No. 5,026,364, entitled "Absorbent Article Having Unitary Waistcap and Waistband", issued to Robertson on Jun. 25, 1991; and which is incorporated herein by reference. The elastomeric layer is preferably an elastomeric film such as that marketed by Exxon Chemical under the name Exxon 500 which is stretched to between about 50% and 100% prestrain. When operatively joined to the topsheet in the central panel of the pull-on diaper, the unitary waistcap/waistband in conjunction with the underlying layers of the pull-on diaper provide extension forces, when stretched to 67% (1 inch in this particular embodiment) extension, preferably between about 100 grams/in and 300 grams/in, more preferably between about 150 grams/in and about 200 grams/in. The unitary waistcap/waistband, in this preferred embodiment, also provides at least 37 mm (1½ inches) of contraction (i.e., 76 mm (3 inches) of contraction in the entire product) to provide a tapered fit at the upper part of the pull-on diaper.

In a particularly preferred embodiment, the unitary waistcap/waistband is breathable to allow water vapor to escape from the front region and the back region of the pull-on diaper. Breathability may be provided in the unitary waistcap/waistband by selecting relative breathable materials for its construction and/or by aperturing or venting the waistcap/waistband such as is discussed herein with respect to the stretch laminates in the side panels.

The medial panels 62 and 62' of the belt 38 are not gathered in order to not bunch or bind the absorbent core 84 during use. In the embodiments shown in FIGS. 1–4, the medial panels 62 and 62' are also preferably not extensible to maintain the integrity of the absorbent core 84. Alternatively, the medial panels can be rendered elastically extensible, but not gathered, by using extensible but uncontracted materials to form the medial panel. For example, the medial panel could comprise a zero strain stretch laminate as used herein for the side panels or it could comprise the structural elastic-like film (SELF) webs as described in the previously referenced WO 95/03765, which is incorporated herein by reference. If the medial panel is made extensible, it is preferred to allow the absorbent core to "float" (not secure the absorbent core to the medial panel) to maintain the integrity of the absorbent core and to not restrict the extension of the medial panel.

The seam panels 66 and 66' are those portions of the belt 38 designed to be seamed or bonded together by the manufacturer to form the defined waist opening 36 and leg openings 34. As shown in FIG. 1A, the seam panels 66 and 66' extend laterally outwardly from the respective side panels 64 and 64' to the side edge 72 or 72' and generally longitudinally extend from the end edge 70 or 70' to the leg edge 71 or 71', respectively. The seam panels are preferably an extension of the chassis layer and other elements such as the belt layers and the topsheet, or any other combination of these elements. In a preferred embodiment, each seam panel is formed by portions of the chassis layer, the belt layers, the elastic panel members, and the barrier layers of the topsheet. (In the seam panel, the stretch laminate is preferably not activated by mechanical stretching, although it may be, if desired, to provide additional extensibility in this region.)

Referring to FIG. 1, the seams 32 are preferably formed by bonding together the seam panels 66 of the front region 26 with the seam panels 66' of the back region 28. The seams 32 can be formed in a number of different ways. For example, the seams can be formed by bonding together portions of outwardly extending seam panels to form an outwardly extending fin seam, bonding together portions of inwardly extending seam panels to form an inwardly extending fin seam, the seam panels may be overlapped and bonded together to form lap seams, or the seam panels may be bonded together using any other seam configurations that are known in the art, such as a flangeless side seam. An example of a flangeless seam is disclosed in U.S. Pat. No. 5,236,430 entitled "Disposable Training Pant Having Fusion-Slit Side Seams" issued to Russell P. Bridges on Aug. 17, 1993, which patent is incorporated herein by reference. The bonding of the seams of the present invention can be by any suitable means well known in the art appropriate for the specific materials employed in the seam panels. Thus, sonic sealing, heat sealing, pressure bonding, adhesive bonding, sewing, autogeneous bonding, and the like may be appropriate techniques.

Figure 11:
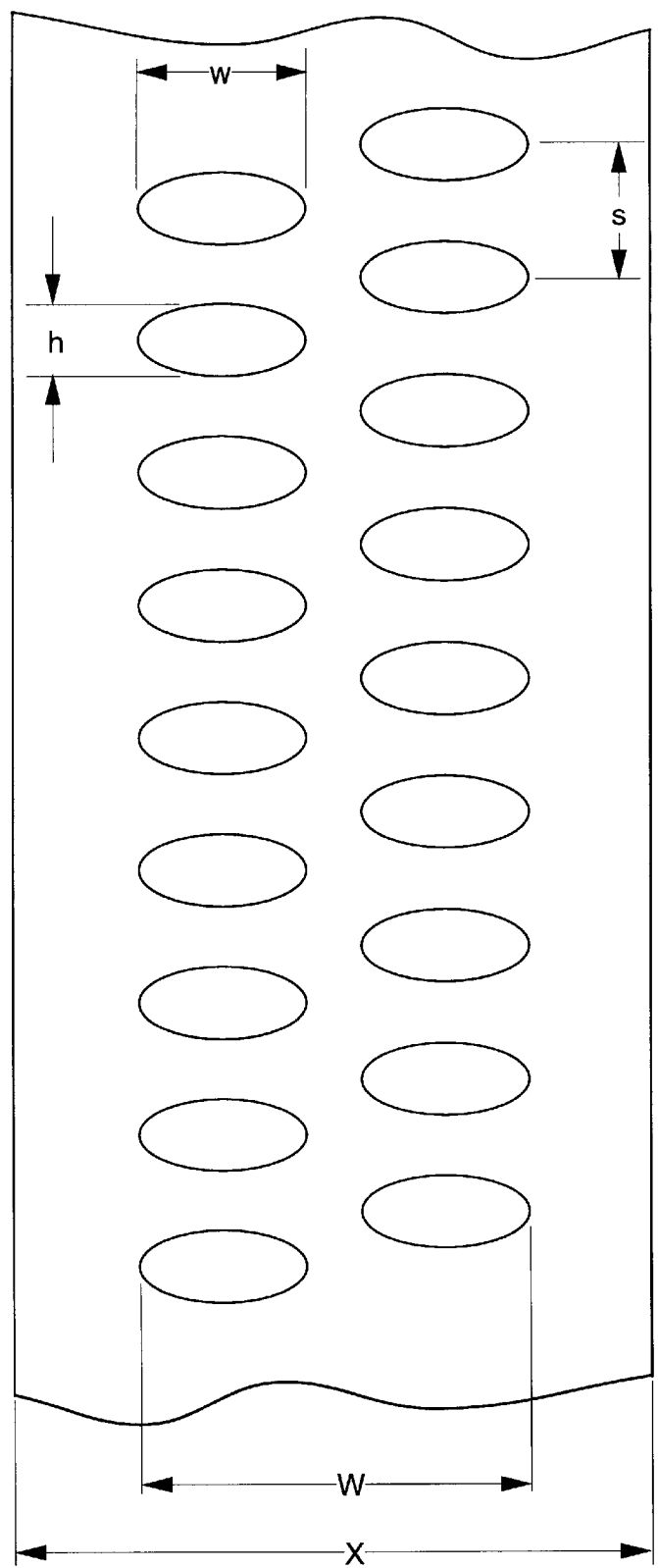
FIG. 11 is a plan view of a seam pattern of the present invention.

In a preferred embodiment of the present invention, the pull-on diaper 20 is formed by overlapping the seam panels 66 of the front region 26 with the seam panels 66' of the back region 28 to form a lap seam. The seam panels are preferably joined by a pattern of heat/pressure or ultrasonic welds such as is shown in FIG. 11. In this particular seam, the bonding pattern comprises two rows of elliptical bonds. The total bond seam width, W, is about 6 mm (about 0.240 in) based upon a total overlap, X, of the seam panels of about 11 mm (about 0.4375 in). Each bond is about 2.5 mm (about 0.1 in) wide, w, and about 1 mm (about 0.04 in) high, h. The bonds are spaced from each other in each row, s, by about 2 mm (about 0.08 in) center to center. Alternative patterns, dimensions, and spacing are also contemplated. With the fusion of the first belt layer 42, a portion of the chassis layer 40, a portion of the elastic panel member 78 in the side panels in the front region, a portion of the barrier layer 88, the second belt layer 44, a second portion of the chassis layer 40, a portion of the elastic panel member 78' in the side panels in the back region, and a second portion of the barrier layer 88, the seam 32 is very strong and will not rip or tear during application or wearing of the pull-on diaper 20.

A potentially strong seam may be produced by increasing certain amounts of polymeric material in the seam panels. The amount of polymeric material in the seam panels can be increased by using higher basis weight nonwoven materials, thicker plastic films, or by introducing additional layers of materials to the seam panels. For example, additional plastic films or nonwoven webs may be joined in the seam panels. Alternatively, the layers forming the diaper may be extended beyond the intended area of seaming and folded back into the seam panel to introduce additional strata in the seam panels. Examples of these types of seams are discussed in the above-referenced U.S. Pat. No. 5,236,430.

Besides the continuous belt 38, the pull-on diaper 20 comprises a chassis assembly (main panel 56 and leg flap panels 58) extending between the legs of the wearer to thereby define the crotch region 30. The crotch region 30 typically comprises at least an outer covering layer, preferably also an absorbent core 84. In the embodiment shown in FIGS. 1–4, the outer covering layer comprises the chassis layer 40 and the topsheet 80. The chassis assembly further preferably comprises the elastic leg features 52.

The elastic leg features 52 provide improved containment of liquids and other body exudates in the crotch region 30 and about the leg openings in general. Each elastic leg feature 52 may comprise several different embodiments for reducing the leakage of body exudates in the leg flap panels 58 (the elastic leg feature can be and is sometimes also referred to as leg bands, side flaps, barrier cuffs, or elastic cuffs.) U.S. Pat. No. 3,860,003 entitled "Contractable Side Portions For A Disposable Diaper" issued to Buell on Jan. 14, 1975 describes a disposable diaper which provides a contractible leg opening having a side flap and one or more elastic panel members to provide an elasticized leg cuff (gasketing cuff). U.S. Pat. No. 4,909,803 entitled "Disposable Absorbent Article Having Elasticized Flaps" issued to Aziz and Blancy on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,795,454, entitled "Absorbent Article Having Leakage-Resistant Dual Cuffs" issued to Dragoo on Jan. 3, 1989 discloses a disposable diaper having leakage resistant dual cuffs wherein the topsheet stops short of the side edge of the diaper to prevent wicking out to the side of the garment. Each of these patents are incorporated herein by reference. While each elastic leg feature may be configured so as to be similar to any of the leg bands, side flaps, barrier cuffs or elastic cuffs described above, it is preferred that each elastic leg feature comprise a combination of a gasketing cuff and a barrier cuff. The gasketing cuff and barrier cuffs are preferably formed as shown in the Dragoo patent and as discussed herein.

In an alternative embodiment of the present invention, the leg flap panels 58 can further comprise a structural elastic-like film (SELF) web as described in the above referenced WO 95/03765. The SELF web of the leg flap panels provides extensibility in the lateral direction. By providing a SELF web next to, over, or outside of the elastic leg members forming the gasketing cuff, the pull-on diaper is provided with an area adjacent the legs which can expand when needed for additional void volume due to heavy loading, and also to provide a snug fit to reduce the possibility of leakage in the leg regions due to gapping. As the diaper is loaded and gets heavier, the weight forces cause the extensible leg flap panels to expand in the lateral direction thereby reducing gapping at the legs due to this expansion instead of the cuff being pulled downward by the weight and gapping away from the leg. The result is that action of the gasketing cuff is independent from the absorbent core thus providing better fit and containment. Additionally, the SELF web enhances the softness of the product in the gasketing cuff and contributes to overall baby friendly aesthetics. In fact, the main panel, may if desired, comprise a SELF web to provide softness and containment characteristics. Alternatively, the leg flap panels may comprise a SELF web or a mechanically stretched laminate that is extensible in the longitudinal direction to permit extension of the leg openings in the longitudinal direction thereby fitting wearers having larger legs.

The absorbent core 84 is preferably positioned adjacent the inner surface 76 of the chassis layer 40 and is preferably joined thereto by attachment means (not shown) such as those well known in the art. For example, the chassis layer may be secured to the absorbent core by a uniform continuous layer of adhesive, a patterned layer of adhesive, or an array of separate lines, spirals, or spots of adhesive. Adhesives which have been found to be satisfactory are manufactured by Findley Adhesives of Wauwautosa, Wis., and marketed as Findley H2120. The attachment means preferably comprises an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The absorbent core 84 may be any absorbent means which is generally compressible, conformable, non-irritating to the wearer's skin, and capable of absorbing and retaining liquids such as urine and other certain body exudates. The absorbent core may be manufactured in a variety of sizes and shapes (e.g., rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core may also be varied (e.g., the absorbent core may have varying caliper zones, hydrophilic gradients, superabsorbent gradients, or lower average density and lower average basis weight acquisition zones; or may comprise one or more layers or structures). The total absorbent capacity of the absorbent core should, however, be compatible with the design loading and the intended use of the pull-on diaper. Further, the size and absorbent capacity of the absorbent core may be varied to accommodate wearers ranging from infants through adults.

A preferred embodiment of the absorbent core has an asymmetric, modified hourglass shape and has a body surface toward the body of the wearer (inner surface) and a garment surface opposite the body surface. An exemplary absorbent structure for use as the absorbent core of the present invention that has achieved wide acceptance and commercial success is described in U.S. Pat. No. 5,360,420 entitled "Absorbent Structures Containing Stiffened Fibers and Superabsorbent Material" issued to Cook, Lash, Moore, & Young on Nov. 1, 1994. These references are incorporated herein by reference. Preferably, the absorbent core will comprise an acquisition/distribution layer of chemically stiffened cellulosic fibers and a storage layer positioned beneath the acquisition/distribution layer comprising a mixture of wood pulp fibers and superabsorbent material such as are disclosed in U.S. Pat. No. 4,610,678 entitled "High-Density Absorbent Structures" issued to Weisman and Goldman on Sep. 9, 1986, and incorporated herein by reference.

The topsheet 80 is positioned adjacent the body surface of the absorbent core 84 and is preferably joined to the absorbent core 84 and the chassis layer 40 by attachment means (not shown) such as those well known in the art. Suitable attachment means are described with respect to joining the absorbent core to the chassis layer. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment, the topsheet and the chassis layer are indirectly joined together by directly joining them to the absorbent core or the elastic panel members or other elements of the pull-on diaper.

The topsheet 80 preferably comprises a three member structure such as disclosed in U.S. Pat. No. 4,795,454, entitled "Absorbent Article Having Leakage-Resistant Dual Cuffs" issued to Dragoo on Jan. 3, 1989, which is incorporated herein by reference. As shown in FIG. 4, the topsheet 80 comprises a primary layer 86 and barrier layers 88 joined to and extending laterally outwardly from the primary layer 86. The primary layer 86 is a liquid pervious material allowing liquids to rapidly penetrate through its thickness and be absorbed by the absorbent core. The two barrier layers 88 are preferably hydrophobic to prevent leakage out the sides of the diaper and are more preferably drawable to strengthen the stretch laminates.

The primary layer 86 is preferably compliant, soft feeling, and non-irritating to the wearer's skin. The primary layer is liquid pervious permitting liquids (e.g., urine) to readily penetrate through its thickness. A suitable primary layer may be manufactured from a wide range of materials, such as porous foams; reticulated foams; apertured plastic films or three dimensionally expanded formed films; or woven or nonwoven webs of natural fibers, synthetic fibers, or a combination of natural and synthetic fibers. Preferably, the primary layer is manufactured by Fibertec, Inc. of Landisville, N.J. under the designation 6701.

In the embodiment shown in FIG. 3, the primary layer 86 is preferably noncoterminous with the chassis layer so that liquid will not wick along and through the primary layer to the edges of the pull-on diaper, so that liquids will not wick underneath and beyond the stand-up barrier cuffs formed by the barrier layers, and so that more drawable materials may be positioned in the side panels to produce stronger stretch laminates. The primary layer preferably overlays a major portion of the body surface of the absorbent core, more preferably all of the body surface area of the absorbent core in at least the crotch region, so that exudates that are discharged into the pull-on diaper penetrate through the primary layer where they are absorbed by the absorbent core. The primary layer extends laterally outwardly toward the side edges of the absorbent core, preferably beyond the side edges of the absorbent core in at least the crotch region. The primary layer, however, terminates inwardly of the leg edges of the crotch region. In the most preferred configurations, the primary layer terminates adjacent the proximal edge of the barrier layer (i.e., the terminating edge of the primary layer is positioned adjacent the proximal edge) or the terminating edge is positioned remotely from and inboard of the proximal edge. Adjacent is used in this context to mean that the primary layer terminates at the proximal edge plus or minus small areas of the primary layer material that may extend inside or beyond the proximal edge due to machine tolerances during manufacture or variations in the area of the primary layer when it is manufactured.

In the preferred embodiment of the topsheet 80 shown in FIG. 3, the barrier layers 88 form the elastic leg features 52 (preferably, a gasketing cuff and/or a barrier cuff) and, preferably, a portion of the stretch laminates.

In order to form the gasketing/barrier cuff elastic leg feature as shown in FIG. 3, the barrier layer 88 preferably has a flap portion 90 and a stand-up (channel) portion 92. The stand-up portion 92 has a proximal edge 95 and a distal edge 95'. While the flap portion 90 is preferably a continuous segment of the barrier layer 88, the flap portion 90 may be formed from a different piece of material secured to the stand-up portion 92 so that the flap portion 90 could have different physical properties, dimensions, and characteristics than the stand-up portion 92. In fact, the flap portion, or the stand-up portion, may be omitted entirely from the diaper if desired. The stand-up portion 92 forms and defines the flap of the barrier cuff as described in U.S. Pat. No. 4,795,454 (Dragoo). The proximal edge 95 of the stand-up portion is preferably disposed between the elastic leg members 96 and the longitudinal centerline, most preferably between the elastic leg members 96 and the side edge of the absorbent core 84 in at least the crotch region 30 to create a seal along the proximal edge. The distal edge 95' is preferably not secured to any underlying elements of the pull-on diaper in at least the crotch region 30 to form the stand-up barrier cuff. The ends of the stand-up portion are preferably joined to the underlying structure of the pull-on diaper, the primary layer, by closing means 98, such as any of the attachment means herein described, to enhance the stand-up function of the barrier cuffs. The stand-up portion 92 of the barrier layer 88 is thus preferably hydrophobic so as to reduce leakage of exudates from the pull-on diaper.

In a preferred embodiment of the present invention, at least some segment of the flap portion 90 of the barrier layer 88 in the front region 26 and in the back region 28 is subjected to mechanical stretching in order to provide the stretch laminates in the side panels 64 and 64', respectively. Thus, at least the flap portion 90, preferably the entire barrier layer 88, is elongatable, more preferably drawable (but not necessarily elastomeric), so that the barrier layer will, upon mechanical stretching be at least to a degree permanently elongated such that it will not fully return to its original configuration. In especially preferred embodiments, the barrier layers can be subjected to mechanical stretching without undue rupturing or tearing. Thus, the barrier layers are preferably elongatable, more preferably drawable, and most preferably hydrophobic materials. Suitable materials for the barrier layers include many of the layers suitable for the belt layers. A preferred material for the barrier layers comprises a spun-bonded polyethylene or polyethylene blended fiber web. A suitable material for the barrier layer is the spun-bonded polyethylene fiber web manufactured by Fiberweb N.A. of Simpsonville, N.C. under the designation E1004203.

The pull-on diaper 20 can also preferably provided with vents or apertures to permit the passage of air and water vapor to and from the interior of the pull-on diaper. In a preferred embodiment, the apertures are positioned in the side panels. In this configuration, exudates are prevented from leaking out of the areas adjacent the absorbent core but air and water vapor are allowed to be exchanged in the product to ventilate it so that the product does not become excessively wetted by body perspiration and uncomfortable to wear. Vents may additionally be provided in other panels of the pull-on product or on certain of the features of the pull-on diaper. For example, vents may be provided in the waistband panel in the front region or the back region to provide ventilation and breathability in the waistband regions and/or vents may be provided in the unitary waistcap/waistband to further enhance ventilation in the product.

The pull-on diaper would preferably have a plurality of vents within the side panels, the vents being arranged in a defined pattern of large and small apertures. The apertures are generally in the range of about 0.3–2.5 mm in diameter, with the larger apertures being preferably in the range of about 1–2 mm and the smaller apertures being in the range of about 0.5–0.9 mm in diameter. The apertures can be formed by punching holes or apertures into the fabric or by forming holes by autogeneous bonds such as ultrasonic or thermal/pressure techniques. Such apertures and forming techniques are described in U.S. Pat. No. 2,544,069 issued to Cutler on Mar. 6, 1951; and U.S. Pat. No. 4,834,738 issued to Kielpikowski et al. on May 30, 1989; each of which is incorporated herein by reference. Preferably, the apertures extend through all of the layers of the product, all of the layers of the stretch laminates in the side panels, such that the vents extend from the inside to the outside of the product. Alternatively, the vents may only be made in one or more of the layers or they may comprise slits or cuts rather than holes.

Breathability may alternatively be provided by making the materials of the pull-on diaper out of air or vapor permeable materials such as are known in the art. For example, the chassis layer could comprise a breathable (vapor permeable) but liquid impervious plastic film. The elastic panel members may be open material such as foams, scrims, nonwovens, or breathable elastomeric films to further enhance the breathability of the pull-on diaper.

The pull-on diaper 20 of the present invention can be applied by a caregiver or be self-applied by the wearer. Typically, the waist opening 36 will be expanded to allow the wearer to insert one of their feet into one of the leg openings 34. The other foot is then inserted into the other leg opening 34. The pull-on diaper 20 is then pulled up over the torso of the wearer into its wearing position. The force wall created by the stretch laminates especially assists in self application of the pull-on diaper by forcing the product to be pulled up over the buttocks rather than further expanding. The pull-on diaper is then worn and can contain and hold discharged body exudates. The pull-on diaper is removed from the wearer by either pulling it back down over the legs or tearing the portions of the pull-on diaper adjacent the seams.

Figure 5:
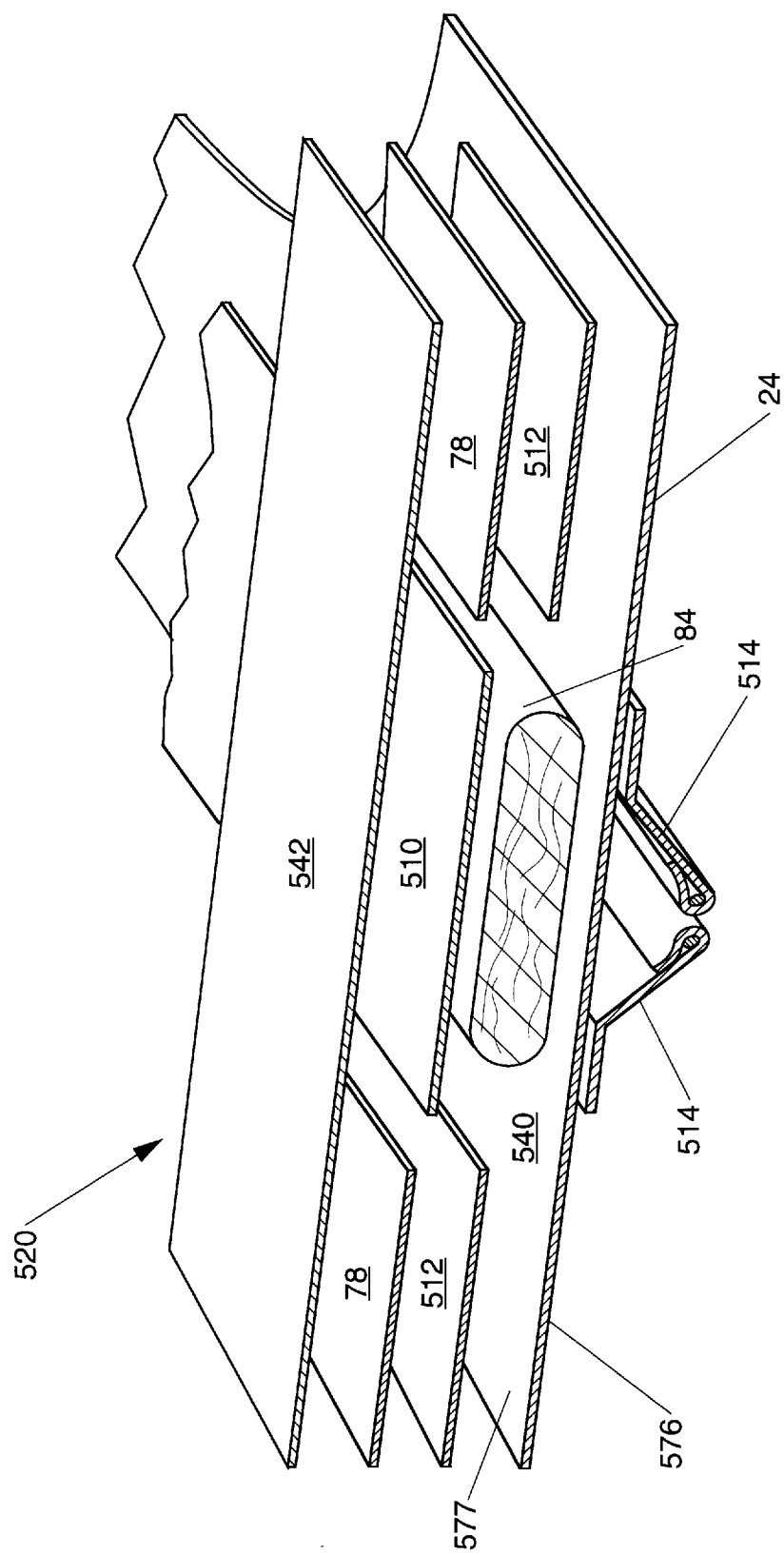
FIG. 5 is a cross-sectional perspective view of an alternative embodiment of the pull-on garment of the present invention.

FIG. 5 shows a perspective cross-sectional view of an alternative embodiment of the pull-on diaper of the present invention. As shown in FIG. 5, the chassis layer 540 forms the inner surface 24 of the pull-on diaper 520. The chassis layer 540 thus serves as the topsheet. For this reason, in this embodiment, the chassis layer 540 preferably comprises a liquid pervious nonwoven web. The chassis layer 540 is preferably the nonwoven material discussed previously herein with respect to the formation of the primary layer of the topsheet. The first belt layer 542 is positioned adjacent the outer surface 577 of the chassis layer 540. The second belt layer (not shown) also is positioned adjacent the outer surface of the chassis layer. Additionally, a central backsheet layer 510, preferably comprising a liquid impervious plastic film, is positioned on the inner surface of the first belt layer 542, on the outer surface 577 of the chassis layer 40, so as to act as a backsheet for the pull-on diaper. The elastic panel members 78 are positioned between the chassis layer 540 and the first belt layer 542 to form the front stretch laminates. The absorbent core 84 is preferably positioned on the outer surface 577 of the chassis layer 540, preferably between the chassis layer 540 and the central backsheet layer 510. The barrier cuffs 514 of the elastic leg feature preferably comprise a relatively narrow strip of material (a barrier flap) joined to the inner surface 576 of the chassis layer 540 such as is shown in the above referenced U.S. Pat. No. 4,695,278 to Lawson. The flaps of the barrier cuffs may comprise a nonwoven web, a plastic film, or a laminate of a nonwoven web and a plastic film.

As shown in FIG. 5, the stretch laminates additionally comprise a reinforcement layer 512 preferably positioned between the chassis layer 540 and the elastic panel member 78. The reinforcement layer 512 acts to "strain reinforce" the stretch laminates to allow the deep mechanical stretching (straining) of the stretch laminate without creating local tears or holes in the stretch laminate. As previously discussed, some materials are more strainable than other materials, especially at the high straining forces encountered by the mechanical stretching operation done on the stretch laminates. Thus, the joinder of a more strainable material with a less strainable material results in a combination laminate that will be strainable to such a high degree without undue tearing or ripping of the materials. This is especially important in the present embodiment where the chassis layer 540 comprises a nonwoven fabric. Since the chassis layer 540 acts as the topsheet for the pull-on diaper 520, the chassis layer 540 will typically comprise a nonwoven material which is readily liquid pervious but which is generally not as drawable as other nonwoven materials. Thus, the chassis layer 540 of this embodiment will tend to shred or tear when it undergoes the mechanical stretching operation to form the stretch laminates. The reinforcing layer 512, which is a more drawable material than the chassis layer 540, when laminated to the chassis layer 540 prior to mechanical stretching, bridges or spans the tears in the chassis layer 540 to allow the overall stretch laminate to not fail or have holes during use.

The reinforcing layer 512 may thus comprise a number of materials that are drawable to provide the necessary strength in the stretch laminate. Examples of such reinforcing layers include plastic films, apertured plastic films such as DRI-WEAVE marketed by The Procter & Gamble Company, or nonwoven webs. Preferably, in order to provide breathability in the stretch laminates, the reinforcing layer comprises an apertured plastic film or a nonwoven material. More preferably, the reinforcing layer comprises those nonwovens useful as the belt layers and described herein.

As previously discussed, the reinforcing layers are preferably positioned adjacent the weaker layers to provide them with strength. In the embodiment shown in FIG. 5, the reinforcing layer 512 is preferably positioned on the outer surface 577 of the chassis layer 540 although it may be positioned on the inner surface of the chassis layer 540 if desired. Additional reinforcement layers may be provided in the stretch laminates and positioned adjacent any of the elements thereof.

Figure 6:
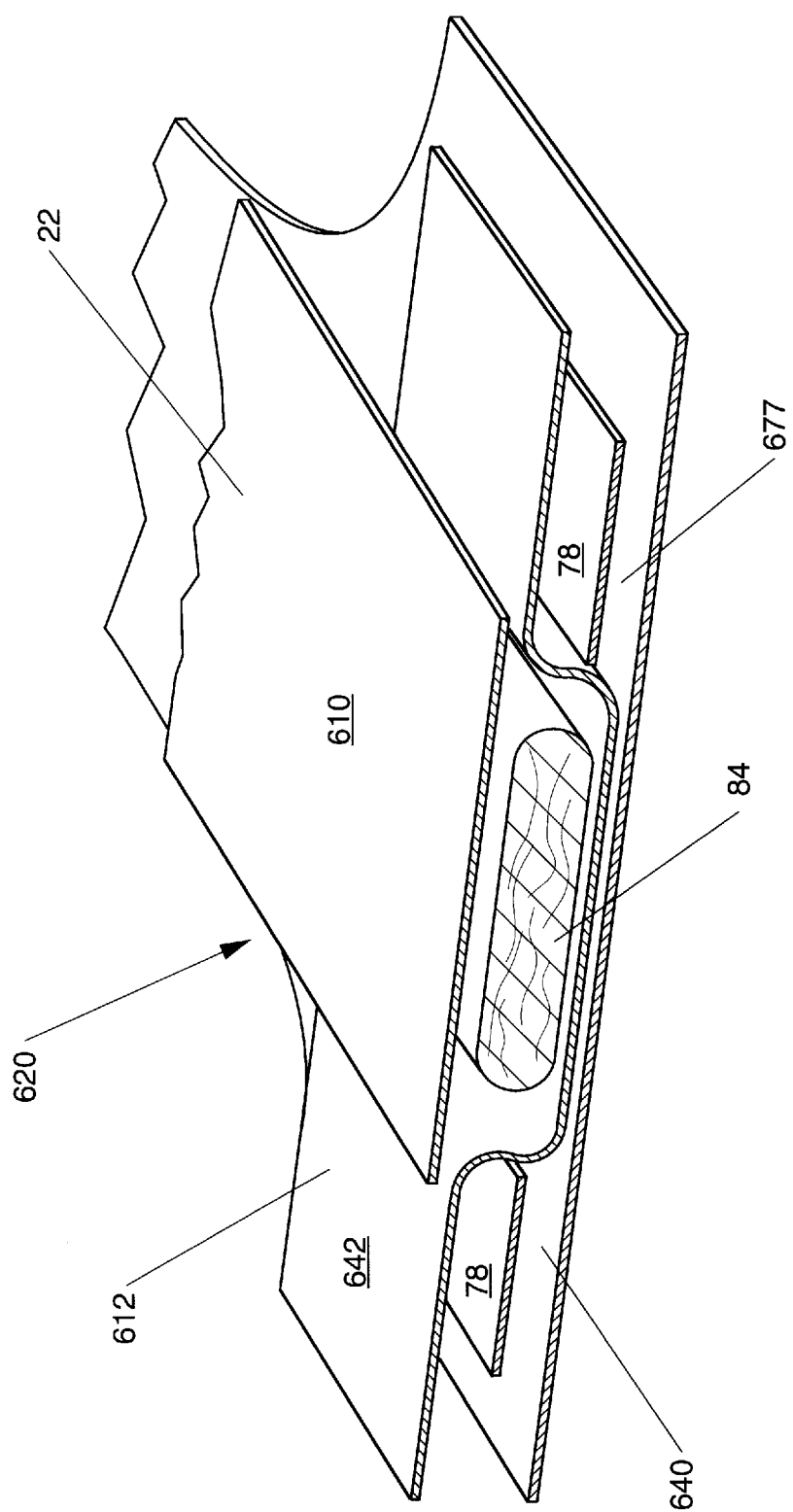
FIG. 6 is a cross-sectional perspective view of a further alternative embodiment of the pull-on garment of the present invention.

FIG. 6 shows an alternative embodiment of the pull-on diaper shown in FIG. 5. The chassis layer 640 functions as the topsheet. The first belt layer 642 is positioned on the outer surface 677 of the chassis layer 640, preferably directly adjacent the chassis layer 640 in the central panel. The elastic panel members 78 are positioned between the first belt layer 642 and the chassis layer 640 in the side panels. Thus, a continuous belt is formed without intervening elements. Forces may thus be distributed and transmitted continuously about the waist opening. A central backsheet layer 610 is positioned on the outer surface 612 of the first belt layer 642 and forms the outer surface 22 of the pull-on diaper 620 in the crotch region and in the central panel of the front region and the back region. The absorbent core 84 is positioned between the central backsheet layer 610 and the first belt layer 642. Since the first belt layer 642 extends over the surface of the absorbent core 84, the first belt layer 642 is also preferably liquid pervious. The first belt layer 642 may thus comprise the spun bonded polyethylene fiber nonwoven material previously discussed herein; however, it is rendered sufficiently fluid pervious such as by adding a suitable surfactant. One or more reinforcement layers may also be positioned in the side panels to prevent undue ripping or tearing of both the chassis layer 640 and the first belt layer 642.

Figure 7:
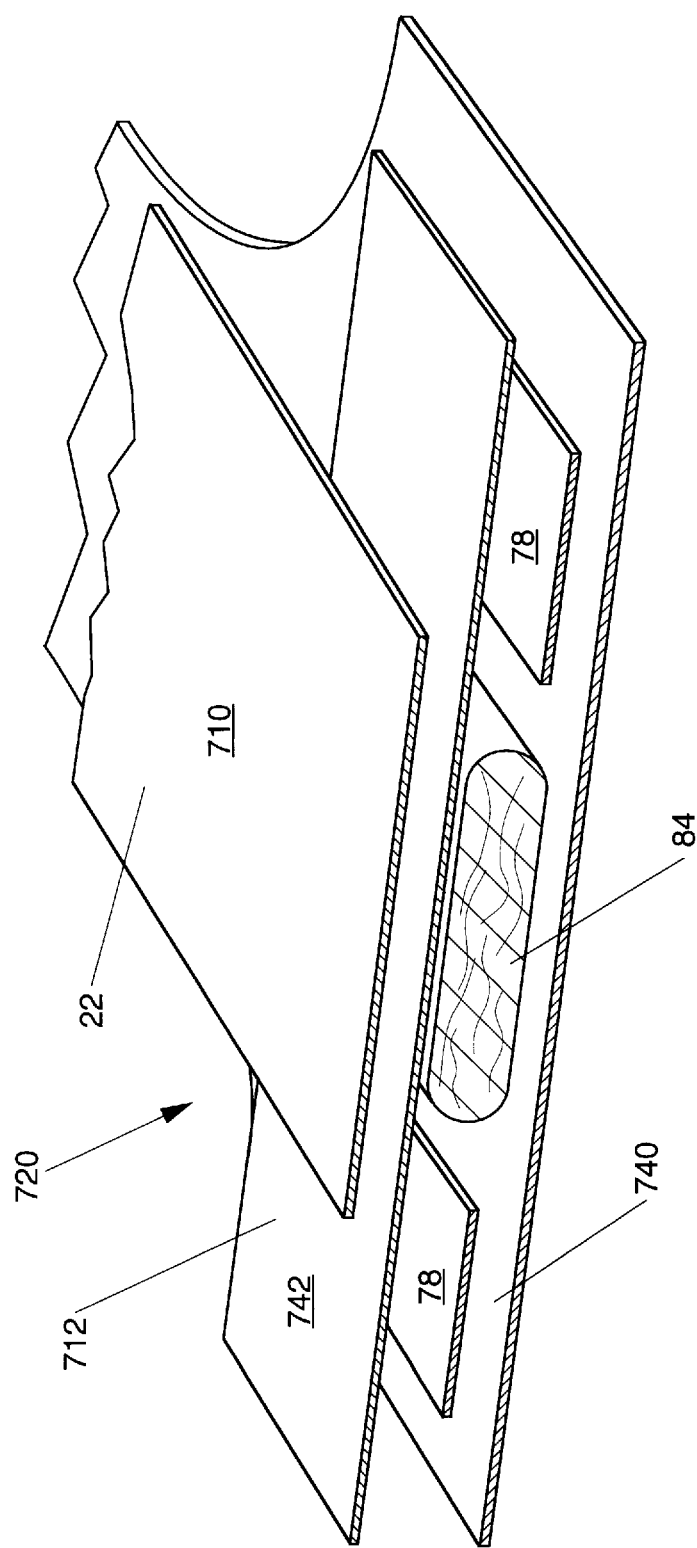
FIG. 7 is a cross-sectional perspective view of a still further alternative embodiment of the pull-on garment of the present invention.

FIG. 7 is a perspective cross-sectional view of a further alternative embodiment of the pull-on diaper shown in FIG. 5. In this embodiment, the absorbent core 84 is positioned between the chassis layer 740 and the first belt layer 742. Since the first belt layer 742 need not be liquid pervious since it is positioned on the garment surface of the absorbent core 84, the first belt layer 742 is preferably drawable and comprises the materials previously described herein for use as the belt layers. The central backsheet layer 710 is positioned on the outer surface 712 of the first belt layer 742 to form the outer surface 22 of the pull-on diaper 720 in the crotch region and in the central panel of the front region and the back region. A reinforcement layer (not shown) may also be positioned between the chassis layer 740 and the elastic panel member 78 to reinforce the chassis layer 740.

Figure 8:
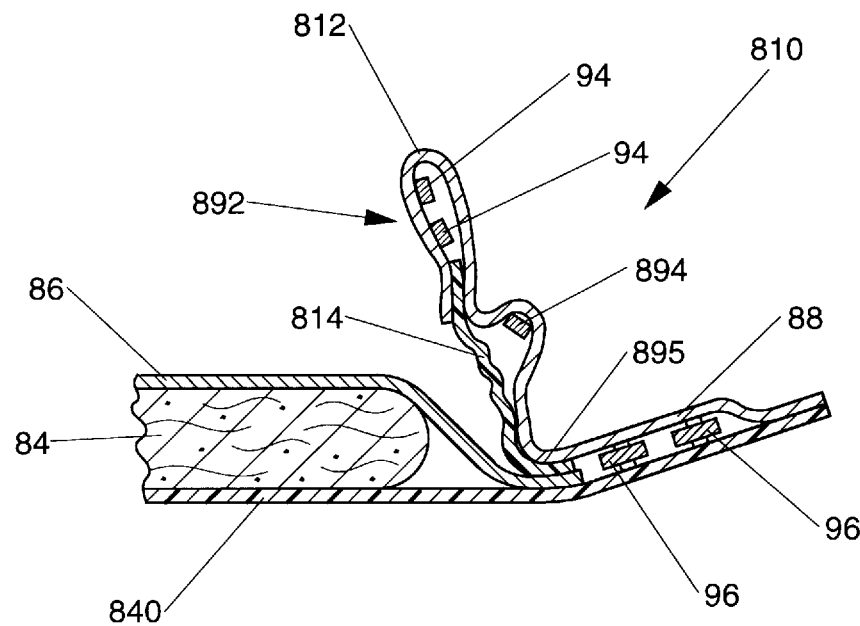
FIG. 8 is a fragmentary cross-sectional view of an alternative elastic leg feature in the crotch region for use on the pull-on garment of the present invention.

FIG. 8 is a cross-sectional view of an alternative barrier cuff configuration of the present invention. As shown in FIG. 8, the flap of the barrier cuff 810 comprises the stand-up portion 892 of the barrier layer 88. The barrier cuff 810 has a proximal edge 895 and a distal edge 812. The proximal edge 895 is joined to the chassis layer 840 to provide a seal to prevent wicking and leaking of exudates out of the side of the leg openings. The distal edge 812 is formed by folding a portion of the barrier layer 88 onto itself and around the elastic spacing members 94. The elastic spacing members 94 are operatively joined to the flap, the barrier layer 88, in an elastically contractible condition adjacent said distal edge 812 to cause the distal edge 812 to stand-up away from the primary layer 86. A containment layer 814 is joined to the flap, the barrier layer 88. The containment layer 814 is preferably a liquid impervious film to further prevent leakage through the barrier cuff 810. The containment layer 814 preferably comprises a polyethylene film. The containment layer 814 preferably extends from just laterally outwardly beyond the proximal edge 895 to a point intermediate the proximal edge 895 and the distal edge 812. In the embodiment shown in FIG. 8, the containment layer is positioned between the folded over portions of the flap. The containment layer 814 extends beyond the proximal edge 895 to further provide an impermeable seal at the proximal edge 895. The containment layer 814 preferably does not extend to the distal edge 812 (in this embodiment—about 6.35 mm (about 0.25 in) from the distal edge) to provide a breathable portion adjacent the distal edge 812 to maintain good skin health. Thus, the barrier cuff 810 is liquid and gas impervious at the base of the barrier cuff 810 to prevent leakage while being gas pervious adjacent the distal edge 812 to enhance the softness and breathability of the barrier cuff 810.

A secondary "barrier" is created by a second elastic spacing member 894 operatively joined with said flap intermediate said proximal edge and said distal edge, preferably at least about 12.5 mm (about 0.5 in) from the elastic spacing members 94. The second elastic spacing member 894 is preferably joined to the flap between the flap and the containment layer 814. Since the containment layer is most preferably joined to the flap at spaced apart zones (adjacent the proximal edge 895 and adjacent the folded over portion of the flap) such that an intermediate portion of the containment layer is unsecured to the flap, the second elastic spacing member is preferably joined to the flap adjacent this intermediate portion such that the second spacing elastic member tends to space the flap away from the containment layer 814 to form a pocket. The second elastic spacing member 894 thus provides a more breathable section of flap adjacent the body since only the nonwoven flap contacts the body. The second elastic spacing member 894 is preferably operatively joined with the flap at a lower force than the elastic spacing members 94 so as to not affect the functionality of the elastic spacing member 94 but to space the flap away from the containment layer 814. The second elastic spacing member 894 is operatively joined in an elastically contractible condition, preferably being secured only adjacent its ends such than an intermediate portion is unsecured to the flap (i.e., it is secured in a manner to form a drawstring elastic as is described in U.S. Pat. No. 4,816,025 entitled "Disposable Diaper Having An Improved Leg Conforming Cuff" issued to Richardson on Mar. 28, 1989, which is incorporated herein by reference) to allow the second spacing elastic member 894 to float within the flap, within the space defined by the flap and the containment layer, so as to provide softness and flexibility as well as better breathability/skin health by spacing the breathable nonwoven flap away from the containment layer and contact the body.

Figure 8A:
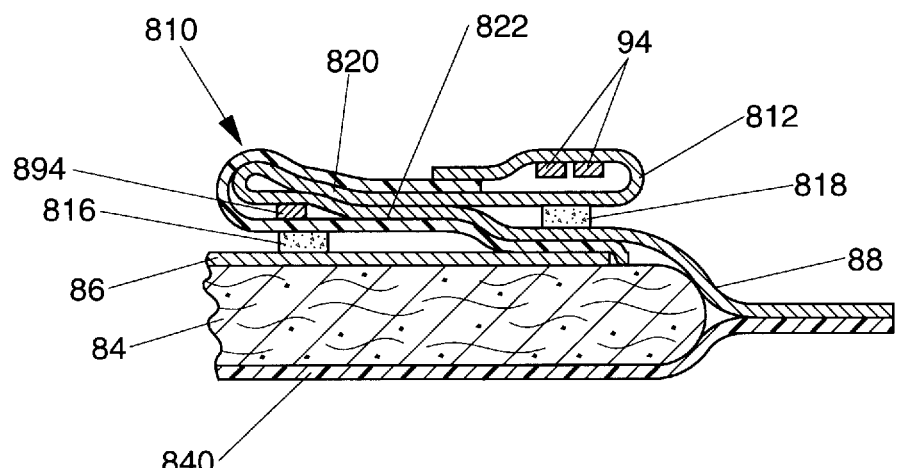
FIG. 8A is a fragmentary cross-sectional view of the elastic leg feature shown in FIG. 8 in the front region.

As a further preferred embodiment to the above barrier cuff embodiment, the cuff height and spacing of the barrier cuffs may be adjusted by the way the barrier cuffs are joined to the pull-on diaper. FIG. 8A shows how the barrier cuff 810 may be joined to the topsheet 80 to optimize the cuff height and cuff spacing. The inner surface of the flap is joined to the diaper, typically the topsheet 80, at its ends laterally inward from the proximal edge by a first closing means 816 at about half the cuff height (adjacent the second elastic spacing member 894). The distal edge 812 is then folded laterally outward back toward the proximal edge such that a first barrier segment 820 and a second barrier segment 822 is formed. The outer surface of the flap in the second barrier segment 822 is joined to the outer surface of the flap in the first barrier segment 820 at the ends of the flap by a second closing means 818. The fold provides a wider cuff spacing and a taller cuff height in the crotch region 30 to significantly improve leakage performance (especially BM containment). It should be noted that the location of the second closing means 818 along the segments can be varied to vary the cuff height and cuff spacing. The cuff height is a particularly important parameter for pull-on garments since the barrier cuff may cause difficulty in application since the wearer's foot may get caught on it. The cuff height is preferably less than about 44.5 mm (about 1.75 in), more preferably between about 31.75 mm and about 44.5 mm (about 1.25 in to about 1.75 in) with the cuff spacing in the crotch region 30 being from about 63.5 mm (about 2.5 in) to about 90 mm (about 3.5 in).

Figure 9:
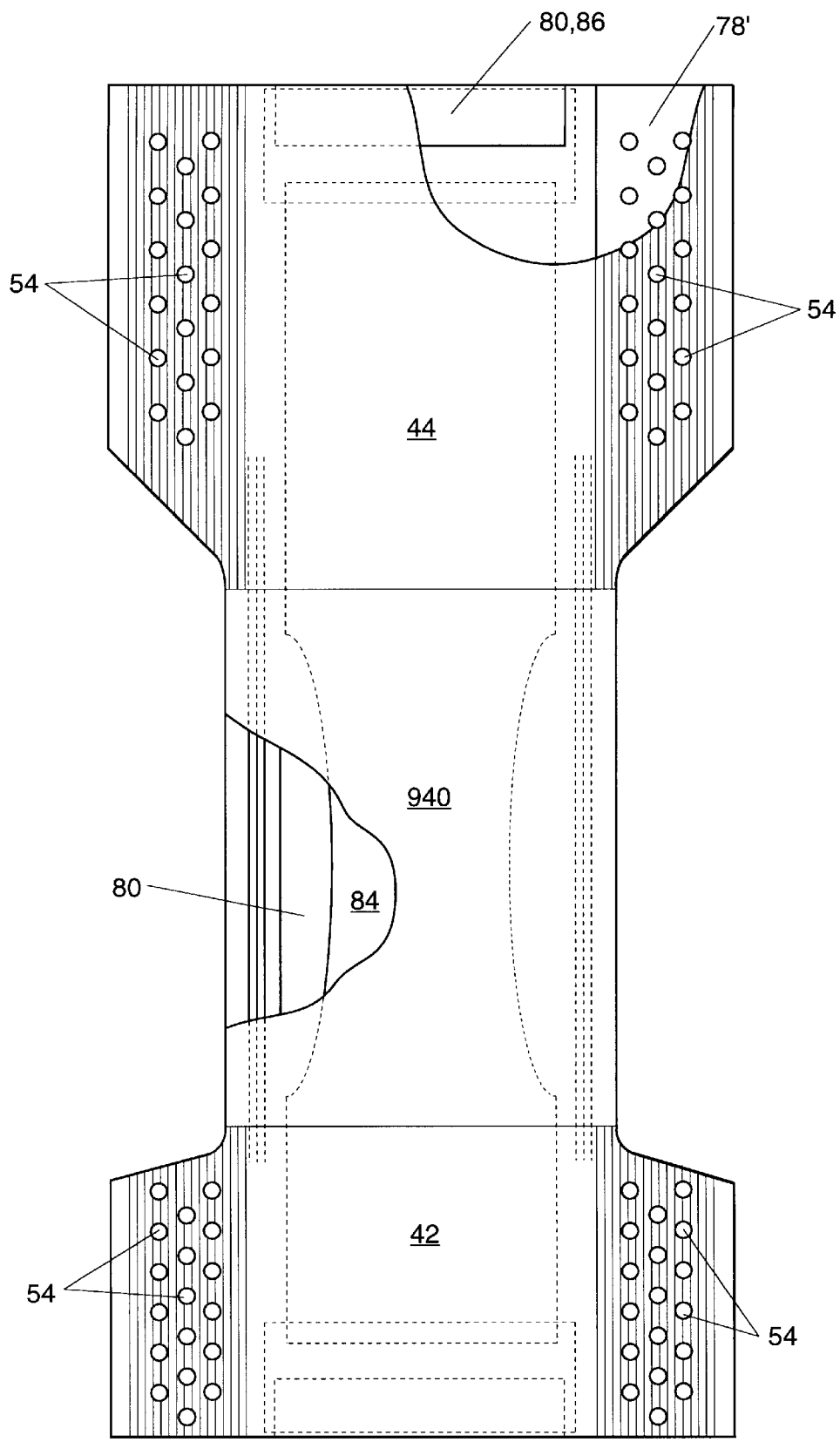
FIG. 9 is a plan view of an alternative embodiment of the present invention wherein the chassis layer has been "windowed" to increase the breathability of the pull-on garment in the waistband panel.

FIG. 9 shows an alternative embodiment of the present invention in which vents 54 are provided in the side panels and a portion of the chassis layer 940 has been removed ("windowed") in each waistband panel. This portion of the chassis layer has been removed in order to provide enhanced breathability in the waistband panels 60 and 60'. The belt in the waistband panels thus comprises the respective belt layer (first belt layer 42 or second belt layer 44), the primary layer 86 of the topsheet 80, and in certain segments the unitary waistcap/waistband 82. Since the belt layer and the primary layer of the topsheet are both preferably nonwoven webs, water vapor will be allowed to pass between the interior and exterior of the pull-on diaper, thereby enhancing the overall breathability of the pull-on diaper. The vents 54 are similar to those previously described herein and provide enhanced breathability in the side panels.

Figure 10:
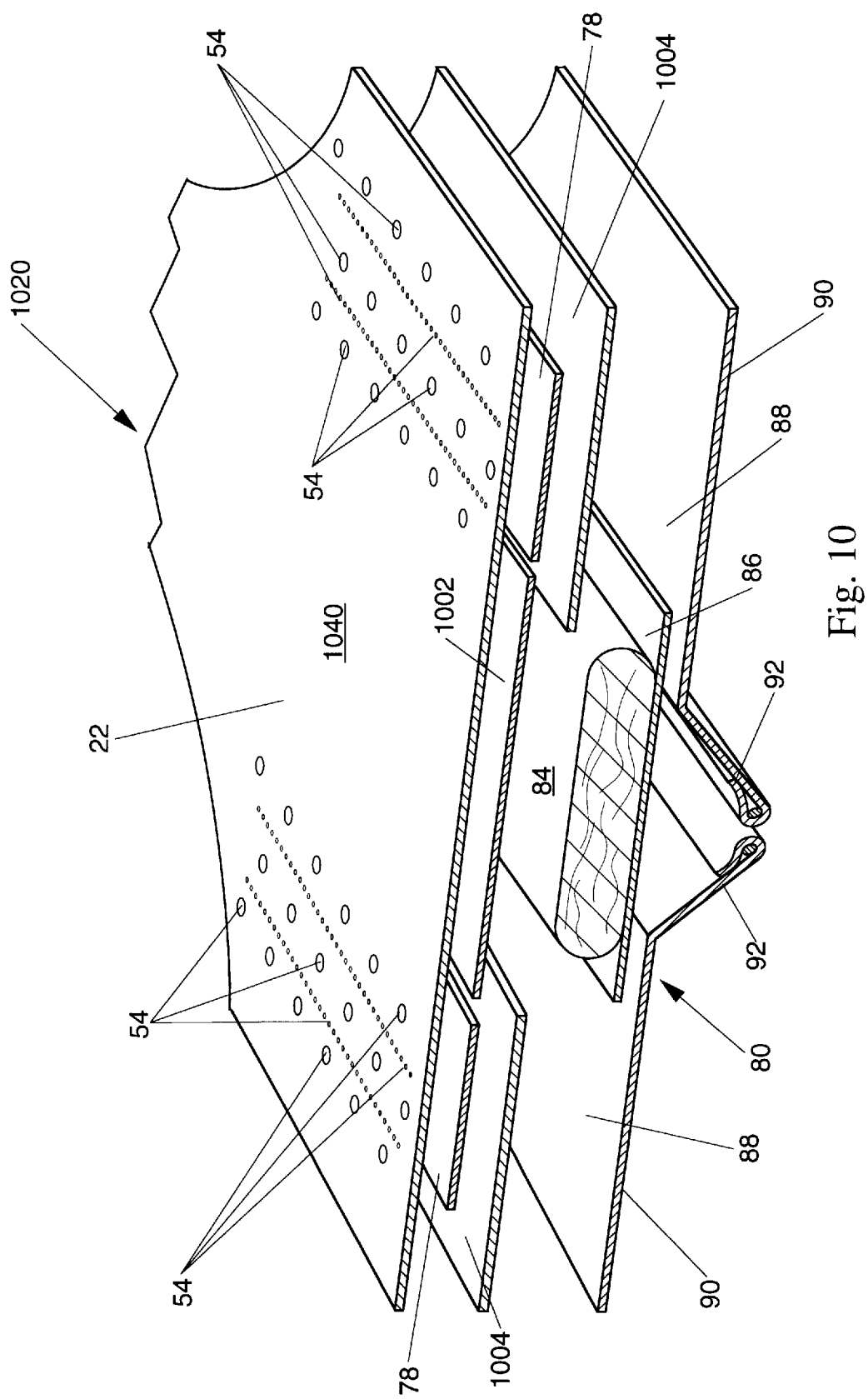
FIG. 10 is a cross-sectional perspective view of a still further alternative embodiment of the pull-on garment of the present invention.

FIG. 10 shows a still further alternative embodiment of the pull-on diaper of the present invention. The chassis layer 1040 also serves as the belt layer. The chassis layer 1040 also provides the outer surface 22 of the pull-on diaper 1020 in both the front region, the back region, and the crotch region. In this embodiment, the chassis layer 1040 preferably comprises a nonwoven web to give the overall pull-on diaper the feel and appearance of a cloth garment. The topsheet 80 comprises a primary layer 86 and a pair of barrier layers 88. In this embodiment, the pull-on diaper 1020 is provided with a composite backsheet that acts as the backsheet for the absorbent core 84 and as reinforcement layers for the stretch laminates in the side panels. In this embodiment, the backsheet comprises a central backsheet layer 1002 and a pair of backsheet reinforcement layers 1004. The central backsheet layer 1002 is preferably a liquid impervious film to contain exudates within the absorbent core 84. However, since the central backsheet layer 1002 need not be subjected to mechanical stretching, it can comprises the liquid impervious, vapor pervious films such as previously described herein to give the product overall breathability in the crotch region and the central panels of the front region and the back region. Since the backsheet reinforcement panels 1004 are subjected to mechanical stretching, they preferably comprise any of the materials suitable for use as a reinforcement layer as previously described herein including nonwoven webs or plastic films. In the embodiment illustrated, the backsheet reinforcement layers 1004 comprise a plastic film such as is used as the chassis layer for the embodiments of FIGS. 1–4. Although it is preferred that the backsheet reinforcement layers overlap with and, more preferably are joined to, the central backsheet layer, the backsheet reinforcement layers may alternatively be spaced laterally outward from and not be secured to the central backsheet layer such that the backsheet reinforcement layers act as independent reinforcement layers. Since both the central backsheet layer 1002 and the backsheet reinforcement layers 1004 preferably each comprise a plastic film, the layers may be joined together prior to being combined into the pull-on diaper for ease of handling during manufacture. The elastic panel members 78 are preferably positioned between the chassis layer 1040 and the backsheet reinforcement layer 1004 to provide the stretch laminates.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable pull-on garment comprising:
   (a) a nonwoven chassis layer comprising a continuous sheet defining
      (i) a front region having an end edge, side edges, leg edges, a central panel comprising a waistband panel and a medial panel, side panels extending laterally outwardly from said central panel, and a seam panel extending laterally outwardly from each said side panel to said side edge, said seam panels and said side panels extending longitudinally from said end edge to said leg edge;
      (ii) a back region opposed to said front region, said back region having an end edge, side edges, leg edges, a central panel comprising a waistband panel and a medial panel, side panels extending laterally outwardly from said central panel to said side edge, and a seam panel extending laterally outwardly from each said side panel to said side edge, said seam panels and said side panels extending longitudinally from said end edge to said leg edge; and
      (iii) a crotch region between said front region and said back region;
   (b) a nonwoven first belt layer positioned so as to extend continuously laterally across said front region from one said side panel to the other said side panel, said first belt layer being joined to said chassis layer;
   (c) a nonwoven second belt layer positioned so as to extend continuously laterally across said back region from one said side panel to the other said side panel, said second belt layer being joined to said chassis layer;
   (d) an elastically extensible breathable front stretch laminate positioned in each said side panel of said front region, each said front stretch laminate comprising a portion of said chassis layer in said side panel, a portion of said first belt layer in said side panel, and an elastic panel member comprising an elastomeric scrim operatively joined with said chassis layer or said first belt layer, each said front stretch laminate being elastically extensible in at least the lateral direction;
   (e) an elastically extensible breathable back stretch laminate positioned in each said side panel of said back region, each said back stretch laminate comprising a portion of said chassis layer in said side panel, a portion of said second belt layer in said side panel, and an elastic panel member comprising an elastomeric scrim operatively joined with said chassis layer or said second belt layer, each said back stretch laminate being elastically extensible in at least the lateral direction; and
   (f) seams joining said front region to said back region adjacent said side edges in said seam panels so as to form two leg openings and a waist opening.

2. The garment of claim 1 additionally comprising a breathable elastic waist feature comprising a unitary waistcap/waistband joined in said waistband panel of said back region, said elastic waist feature being operatively joined in an elastically contractible condition so as to contract said waistband panel.

3. The garment of claim 1 additionally comprising a liquid impervious central backsheet layer joined with said chassis layer.

4. The garment of claim 3 wherein said central backsheet layer comprises a microporous film.

5. The garment of claim 3 wherein said central backsheet layer comprises a plastic film wherein a portion of said central backsheet layer is removed in said waistband panel of said back region.

6. The garment of claim 5 additionally comprising a breathable elastic waist feature comprising a unitary waistcap/waistband joined in said waistband panel of said back region, said elastic waist feature being operatively joined in an elastically contractible condition so as to contract said waistband panel.

7. The garment of claim 6 wherein said unitary waistcap/waistband is apertured.

8. A unitary disposable pull-on garment comprising:
   (a) a chassis layer comprising a continuous sheet comprising a plastic film defining
      (i) a front region having an end edge, side edges, leg edges, a central panel comprising a waistband panel and a medial panel, side panels extending laterally outwardly from said central panel, and a seam panel extending laterally outwardly from each said side panel to said side edge, said seam panels and said side panels extending longitudinally from said end edge to said leg edge;
      (ii) a back region opposed to said front region, said back region having an end edge, side edges, leg edges, a central panel comprising a waistband panel and a medial panel, side panels extending laterally outwardly from said central panel to said side edge, and a seam panel extending laterally outwardly from each said side panel to said side edge, said seam panels and said side panels extending longitudinally from said end edge to said leg edge; and
      (iii) a crotch region between said front region and said back region;
   (b) a first belt layer positioned so as to extend continuously laterally across said front region from one said side panel to the other said side panel, said first belt layer being joined to said chassis layer;
   (c) a second belt layer positioned so as to extend continuously laterally across said back region from one said side panel to the other said side panel, said second belt layer being joined to said chassis layer;
   (d) an elastically extensible breathable front stretch laminate positioned in each said side panel of said front region, each said front stretch laminate comprising a portion of said chassis layer in said side panel, a portion of said first belt layer in said side panel, and an elastic panel member operatively joined with said chassis layer or said first belt layer, each said front stretch laminate being elastically extensible in at least the lateral direction, each said front stretch laminate having apertures to provide breathability;
   (e) an elastically extensible breathable back stretch laminate positioned in each said side panel of said back region, each said back stretch laminate comprising a portion of said chassis layer in said side panel, a portion of said second belt layer in said side panel, and an elastic panel member operatively joined with said chassis layer or said second belt layer, each said back stretch laminate being elastically extensible in at least the lateral direction, each said back stretch laminate having apertures to provide breathability; and (f) seams joining said front region to said back region adjacent said side edges in said seam panels so as to form two leg openings and a waist opening.

9. The garment of claim 8 wherein said apertures in said front stretch laminate and said apertures in said back stretch laminate are arranged in a defined pattern.

10. The garment of claim 9 wherein said pattern comprises large apertures and small apertures.

11. The garment of claim 10 wherein said large apertures and said small apertures are in the range of 0.3 mm to about 2.5 mm.

12. The garment of claim 11 wherein said large apertures are between about 1.0 mm and about 2.0 mm and said small apertures are between about 0.5 mm and about 0.9 mm.

13. The garment of claim 8 wherein a portion of said chassis layer is removed in said waistband panel of said back region.

14. The garment of claim 13 additionally comprising a breathable elastic waist feature comprising a unitary waistcap/waistband joined in said waistband panel of said back region, said elastic waist feature being operatively joined in an elastically contractible condition so as to contract said waistband panel.

15. The garment of claim 14 wherein said unitary waistcap/waistband has apertures.

16. The garment of claim 8 wherein said chassis layer comprises a microporous plastic film.

\* \* \* \* \*